US009227068B2

(12) United States Patent
Ternes et al.

(10) Patent No.: US 9,227,068 B2
(45) Date of Patent: Jan. 5, 2016

(54) CONCURRENT THERAPY DETECTION IN IMPLANTABLE MEDICAL DEVICES

(71) Applicant: Cardiac Pacemakers, Inc., St. Paul, MN (US)

(72) Inventors: David J. Ternes, Roseville, MN (US); Stephen Ruble, Lino Lakes, MN (US); Jason J. Hamann, Blaine, MN (US); Kenneth L. Baker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 154 days.

(21) Appl. No.: 14/013,276

(22) Filed: Aug. 29, 2013

(65) Prior Publication Data
US 2014/0005494 A1 Jan. 2, 2014

Related U.S. Application Data

(62) Division of application No. 12/962,168, filed on Dec. 7, 2010, now Pat. No. 8,548,585.

(60) Provisional application No. 61/267,610, filed on Dec. 8, 2009.

(51) Int. Cl.
*A61N 1/36* (2006.01)
*A61N 1/37* (2006.01)
(Continued)

(52) U.S. Cl.
CPC .......... *A61N 1/36146* (2013.01); *A61B 5/0028* (2013.01); *A61B 5/4848* (2013.01); *A61B 5/7207* (2013.01); *A61N 1/37* (2013.01); *A61N 1/37288* (2013.01)

(58) Field of Classification Search
CPC ...... A61B 5/0028; A61B 5/7207; A61N 1/37; A61N 1/36146; A61N 1/37288
See application file for complete search history.

(56) References Cited

U.S. PATENT DOCUMENTS

| 3,421,511 A | 1/1969 | Schwartz et al. |
| 3,650,277 A | 3/1972 | Sjostrand et al. |
| 4,201,219 A | 5/1980 | Bozal Gonzalez |

(Continued)

FOREIGN PATENT DOCUMENTS

| EP | 0547734 A2 | 6/1993 |
| EP | 1421973 A2 | 5/2004 |

(Continued)

OTHER PUBLICATIONS

"U.S. Appl. No. 11/125,503, Notice of Allowance mailed Jan. 4, 2008", 8 pgs.

(Continued)

*Primary Examiner* — Catherine Voorhees
(74) *Attorney, Agent, or Firm* — Schwegman Lundberg & Woessner P.A.

(57) ABSTRACT

Various method embodiments detect a concurrent therapy, where the concurrent therapy includes a plurality of therapy pulses. Detecting the concurrent therapy includes detecting at least one electrical pulse, extracting at least one characteristic from the at least one electrical pulse, comparing the at least one characteristic of the detected pulse to at least one characteristic of therapy pulses, and detecting that the concurrent therapy is being applied if the at least one characteristic of the detected pulse favorably compares to the at least one characteristic of the therapy pulses.

20 Claims, 10 Drawing Sheets

(51) Int. Cl.
  *A61N 1/372* (2006.01)
  *A61B 5/00* (2006.01)

(56) References Cited

U.S. PATENT DOCUMENTS

| | | | |
|---|---|---|---|
| 4,592,359 A | 6/1986 | Galbraith |
| 4,763,646 A | 8/1988 | Lekholm |
| 4,791,931 A | 12/1988 | Slate |
| 4,960,129 A | 10/1990 | dePaola et al. |
| 5,111,815 A | 5/1992 | Mower |
| 5,199,428 A | 4/1993 | Obel et al. |
| 5,203,326 A | 4/1993 | Collins |
| 5,243,980 A | 9/1993 | Mehra |
| 5,318,592 A | 6/1994 | Schaldach |
| 5,330,507 A | 7/1994 | Schwartz |
| 5,334,221 A | 8/1994 | Bardy |
| 5,356,425 A | 10/1994 | Bardy et al. |
| 5,411,531 A | 5/1995 | Hill et al. |
| 5,437,285 A | 8/1995 | Verrier et al. |
| 5,507,784 A | 4/1996 | Hill et al. |
| 5,522,854 A | 6/1996 | Ideker et al. |
| 5,578,061 A | 11/1996 | Stroetmann et al. |
| 5,626,621 A | 5/1997 | Skoglund et al. |
| 5,658,318 A | 8/1997 | Stroetmann et al. |
| 5,662,689 A | 9/1997 | Elsberry et al. |
| 5,690,681 A | 11/1997 | Geddes et al. |
| 5,700,282 A | 12/1997 | Zabara |
| 5,731,848 A | 3/1998 | Patel et al. |
| 5,792,187 A | 8/1998 | Adams |
| 5,817,131 A | 10/1998 | Elsberry et al. |
| 5,893,881 A | 4/1999 | Elsberry et al. |
| 5,916,239 A | 6/1999 | Geddes et al. |
| 5,928,272 A | 7/1999 | Adkins et al. |
| 6,006,134 A | 12/1999 | Hill et al. |
| 6,058,331 A | 5/2000 | King |
| 6,073,048 A | 6/2000 | Kieval et al. |
| 6,134,470 A | 10/2000 | Hartlaub |
| 6,178,349 B1 | 1/2001 | Kieval |
| 6,240,314 B1 | 5/2001 | Plicchi et al. |
| 6,292,695 B1 | 9/2001 | Webster, Jr. et al. |
| 6,304,772 B1 | 10/2001 | Taha et al. |
| 6,341,236 B1 | 1/2002 | Osorio et al. |
| 6,371,922 B1 | 4/2002 | Baumann et al. |
| 6,400,982 B2 | 6/2002 | Sweeney et al. |
| 6,415,183 B1 | 7/2002 | Scheiner et al. |
| 6,421,557 B1 | 7/2002 | Meyer |
| 6,449,507 B1 | 9/2002 | Hill et al. |
| 6,466,822 B1 | 10/2002 | Pless |
| 6,473,644 B1 | 10/2002 | Terry, Jr. et al. |
| 6,477,404 B1 | 11/2002 | Yonce et al. |
| 6,477,418 B2 | 11/2002 | Plicchi et al. |
| 6,487,450 B1 | 11/2002 | Chen |
| 6,493,585 B2 | 12/2002 | Plicchi et al. |
| 6,511,500 B1 | 1/2003 | Rahme |
| 6,522,926 B1 | 2/2003 | Kieval et al. |
| 6,532,388 B1 | 3/2003 | Hill et al. |
| 6,542,774 B2 | 4/2003 | Hill et al. |
| 6,564,096 B2 | 5/2003 | Mest |
| 6,611,713 B2 | 8/2003 | Schauerte |
| 6,622,041 B2 | 9/2003 | Terry, Jr. et al. |
| 6,628,987 B1 | 9/2003 | Hill et al. |
| 6,668,191 B1 | 12/2003 | Boveja |
| 6,690,974 B2 | 2/2004 | Archer et al. |
| 6,819,953 B2 * | 11/2004 | Yonce et al. ............ 600/510 |
| 6,928,324 B2 | 8/2005 | Park et al. |
| 6,934,583 B2 | 8/2005 | Weinberg et al. |
| 6,937,896 B1 | 8/2005 | Kroll |
| 7,039,466 B1 | 5/2006 | Harrison et al. |
| 7,123,961 B1 | 10/2006 | Kroll et al. |
| 7,123,967 B2 | 10/2006 | Weinberg |
| 7,155,278 B2 | 12/2006 | King et al. |
| 7,260,431 B2 | 8/2007 | Libbus et al. |
| 7,277,761 B2 | 10/2007 | Shelchuk |
| 7,299,086 B2 | 11/2007 | McCabe et al. |
| 7,414,534 B1 * | 8/2008 | Kroll et al. ............ 340/573.1 |
| 7,493,161 B2 | 2/2009 | Libbus et al. |
| 7,542,794 B1 | 6/2009 | Zhang et al. |
| 7,542,800 B2 | 6/2009 | Libbus et al. |
| 7,565,195 B1 | 7/2009 | Kroll et al. |
| 7,570,999 B2 | 8/2009 | Libbus et al. |
| 7,587,238 B2 | 9/2009 | Moffitt et al. |
| 7,657,312 B2 | 2/2010 | Pastore et al. |
| 7,660,628 B2 | 2/2010 | Libbus et al. |
| 7,665,195 B1 | 2/2010 | Vazquez-Perez |
| 7,769,450 B2 | 8/2010 | Libbus et al. |
| 7,769,464 B2 | 8/2010 | Gerber et al. |
| 7,873,413 B2 | 1/2011 | McCabe et al. |
| 8,131,359 B2 | 3/2012 | Libbus et al. |
| 8,260,412 B2 | 9/2012 | Krause et al. |
| 8,406,876 B2 | 3/2013 | McCabe et al. |
| 2002/0026221 A1 | 2/2002 | Hill et al. |
| 2002/0026222 A1 | 2/2002 | Schauerte et al. |
| 2002/0058877 A1 | 5/2002 | Baumann et al. |
| 2002/0107553 A1 | 8/2002 | Hill et al. |
| 2002/0120304 A1 | 8/2002 | Mest |
| 2002/0123769 A1 | 9/2002 | Panken et al. |
| 2002/0143369 A1 | 10/2002 | Hill et al. |
| 2002/0165586 A1 | 11/2002 | Hill et al. |
| 2002/0169485 A1 | 11/2002 | Pless et al. |
| 2003/0004549 A1 | 1/2003 | Hill et al. |
| 2003/0045909 A1 | 3/2003 | Gross et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0078623 A1 | 4/2003 | Weinberg et al. |
| 2003/0078629 A1 | 4/2003 | Chen |
| 2003/0100924 A1 | 5/2003 | Foreman et al. |
| 2003/0149450 A1 | 8/2003 | Mayberg |
| 2003/0153953 A1 | 8/2003 | Park et al. |
| 2003/0181951 A1 | 9/2003 | Cates |
| 2003/0212440 A1 | 11/2003 | Boveja |
| 2003/0212445 A1 | 11/2003 | Weinberg |
| 2003/0229380 A1 | 12/2003 | Adams et al. |
| 2004/0002635 A1 | 1/2004 | Hargrove et al. |
| 2004/0049120 A1 | 3/2004 | Cao et al. |
| 2004/0082980 A1 | 4/2004 | Mouine et al. |
| 2004/0088009 A1 | 5/2004 | Degroot |
| 2004/0102820 A1 | 5/2004 | Mouine et al. |
| 2004/0133248 A1 | 7/2004 | Frei et al. |
| 2004/0138721 A1 | 7/2004 | Osorio et al. |
| 2004/0138724 A1 | 7/2004 | Sieracki et al. |
| 2004/0162594 A1 | 8/2004 | King |
| 2004/0172074 A1 | 9/2004 | Yoshihito |
| 2004/0172075 A1 | 9/2004 | Shafer et al. |
| 2004/0193231 A1 | 9/2004 | David et al. |
| 2004/0199210 A1 | 10/2004 | Shelchuk |
| 2004/0210261 A1 | 10/2004 | King et al. |
| 2004/0215289 A1 | 10/2004 | Fukui |
| 2005/0010263 A1 | 1/2005 | Schauerte |
| 2005/0027321 A1 | 2/2005 | Ferek-Petric |
| 2005/0060001 A1 | 3/2005 | Singhal et al. |
| 2005/0075690 A1 | 4/2005 | Toy et al. |
| 2005/0096705 A1 | 5/2005 | Pastore et al. |
| 2005/0107844 A1 | 5/2005 | Van Den Honert et al. |
| 2005/0143779 A1 | 6/2005 | Libbus |
| 2005/0143785 A1 | 6/2005 | Libbus |
| 2005/0148896 A1 | 7/2005 | Siejko et al. |
| 2005/0149126 A1 | 7/2005 | Libbus |
| 2005/0149127 A1 | 7/2005 | Libbus |
| 2005/0149128 A1 | 7/2005 | Heil, Jr. et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149148 A1 | 7/2005 | King |
| 2005/0149155 A1 | 7/2005 | Scheiner et al. |
| 2005/0149156 A1 | 7/2005 | Libbus et al. |
| 2005/0197674 A1 | 9/2005 | McCabe et al. |
| 2005/0251216 A1 | 11/2005 | Hill et al. |
| 2005/0261741 A1 | 11/2005 | Libbus et al. |
| 2006/0020297 A1 | 1/2006 | Gerber et al. |

(56) References Cited

U.S. PATENT DOCUMENTS

| | | |
|---|---|---|
| 2006/0052831 A1 | 3/2006 | Fukui |
| 2006/0079945 A1 | 4/2006 | Libbus |
| 2006/0095080 A1 | 5/2006 | Libbus et al. |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0167497 A1 | 7/2006 | Armstrong et al. |
| 2006/0173495 A1 | 8/2006 | Armstrong et al. |
| 2006/0206153 A1 | 9/2006 | Libbus et al. |
| 2006/0206154 A1 | 9/2006 | Moffitt et al. |
| 2006/0206158 A1 | 9/2006 | Wu et al. |
| 2006/0206159 A1 | 9/2006 | Moffitt et al. |
| 2006/0217772 A1 | 9/2006 | Libbus et al. |
| 2006/0224188 A1 | 10/2006 | Libbus et al. |
| 2006/0224202 A1 | 10/2006 | Moffitt et al. |
| 2006/0229677 A1 | 10/2006 | Moffitt et al. |
| 2006/0241699 A1 | 10/2006 | Libbus et al. |
| 2006/0241725 A1 | 10/2006 | Libbus |
| 2006/0259083 A1 | 11/2006 | Libbus et al. |
| 2006/0271118 A1 | 11/2006 | Libbus et al. |
| 2007/0021799 A1 | 1/2007 | Kieval et al. |
| 2007/0142864 A1 | 6/2007 | Libbus et al. |
| 2007/0142871 A1 | 6/2007 | Libbus et al. |
| 2008/0015648 A1 | 1/2008 | Libbus et al. |
| 2008/0021504 A1 | 1/2008 | McCabe et al. |
| 2008/0167693 A1 | 7/2008 | Kieval et al. |
| 2008/0200959 A1 | 8/2008 | Libbus et al. |
| 2009/0018596 A1 | 1/2009 | Kieval |
| 2009/0030484 A1 | 1/2009 | Chambers |
| 2009/0228060 A1 | 9/2009 | Libbus et al. |
| 2010/0121399 A1 | 5/2010 | McCabe et al. |
| 2010/0285196 A1 | 11/2010 | Moore et al. |
| 2011/0137360 A1 | 6/2011 | Ternes et al. |
| 2012/0150250 A1 | 6/2012 | Libbus et al. |

FOREIGN PATENT DOCUMENTS

| | | |
|---|---|---|
| EP | 1421973 A3 | 5/2004 |
| EP | 1426078 A1 | 6/2004 |
| JP | 2004173791 A | 6/2004 |
| JP | 2004351122 A | 12/2004 |
| JP | 2005500863 A | 1/2005 |
| WO | WO-9216257 A1 | 10/1992 |
| WO | WO-9904329 | 1/1999 |
| WO | WO-03011388 A2 | 2/2003 |
| WO | WO-03018108 A3 | 3/2003 |
| WO | WO-03076008 A1 | 9/2003 |
| WO | WO-03099377 A1 | 12/2003 |
| WO | WO-2004084993 A1 | 10/2004 |
| WO | WO-2004110549 A2 | 12/2004 |
| WO | WO-2005042091 A1 | 5/2005 |
| WO | WO-2006055436 A1 | 5/2005 |
| WO | WO-2005063332 A1 | 7/2005 |
| WO | WO-2005113066 A1 | 12/2005 |
| WO | WO-2006044025 A1 | 4/2006 |
| WO | WO-2006107675 A1 | 10/2006 |
| WO | WO-2006121929 A1 | 11/2006 |
| WO | WO-2006127248 A1 | 11/2006 |
| WO | WO-2007078410 A1 | 7/2007 |
| WO | WO-2008063396 A1 | 5/2008 |
| WO | WO-2008144354 A1 | 11/2008 |
| WO | WO-2011071896 A1 | 6/2011 |

OTHER PUBLICATIONS

"U.S. Appl. No. 10/746,846, Final Office Action mailed Jan. 23, 2008", 18 pgs.

"U.S. Appl. No. 10/746,846, Final Office Action mailed Feb. 12, 2007", 17 pgs.

"U.S. Appl. No. 10/746,846, Non Final Office Action mailed Apr. 26, 2007", 18 pgs.

"U.S. Appl. No. 10/746,846, Non Final Office Action mailed Jul. 25, 2006", 15 pgs.

"U.S. Appl. No. 10/746,846, Response filed Apr. 17, 2007 to Final Office Action mailed Feb. 12, 2007", 16 pgs.

"U.S. Appl. No. 10/746,846, Response filed Jul. 7, 2006 to Restriction Requirement mailed Jun. 9, 2006", 13 pgs.

"U.S. Appl. No. 10/746,846, Response filed Oct. 26, 2007 to Non Final Office Action mailed Apr. 26, 2007", 11 pgs.

"U.S. Appl. No. 10/746,846, Response filed Nov. 9, 2006 to Non Final Office Action mailed Jul. 25, 2006", 17 pgs.

"U.S. Appl. No. 10/746,846, Restriction Requirement mailed Jun. 9, 2006", 7 pgs.

"U.S. Appl. No. 10/962,845, Appeal Brief mailed Sep. 26, 2007", 33 pgs.

"U.S. Appl. No. 10/962,845, Final Office Action mailed Jan. 26, 2007", 7 pgs.

"U.S. Appl. No. 10/962,845, Non Final Office Action mailed May 12, 2006", 10 pgs.

"U.S. Appl. No. 10/962,845, Preliminary Amendment filed Apr. 25, 2005", 11 pgs.

"U.S. Appl. No. 10/962,845, Response filed Oct. 12, 2006 to Non Final Office Action mailed May 12, 2006", 14 pgs.

"U.S. Appl. No. 11/099,141, Final Office Action mailed Oct. 22, 2007", 9 pgs.

"U.S. Appl. No. 11/099,141, Final Office Action mailed Nov. 7, 2008", 8 pgs.

"U.S. Appl. No. 11/099,141, Non-Final Office Action mailed May 6, 2008", 11 pgs.

"U.S. Appl. No. 11/099,141, Non-Final Office Action mailed May 18, 2007", 8 pgs.

"U.S. Appl. No. 11/099,141, Notice of Allowance mailed Jan. 28, 2009", 4 pgs.

"U.S. Appl. No. 11/099,141, Response filed Jan. 6, 2009 to Final Final Office Action mailed Nov. 7, 2008", 9 pgs.

"U.S. Appl. No. 11/099,141, Response filed Feb. 19, 2008 to Final Office Action mailed Oct. 22, 2007", 13 pgs.

"U.S. Appl. No. 11/099,141, Response filed Apr. 5, 2007 to Restriction Requirement mailed Mar. 6, 2007", 11 pgs.

"U.S. Appl. No. 11/099,141, Response filed Aug. 4, 2008 to Non Final Office Action mailed May 6, 2008", 10 pgs.

"U.S. Appl. No. 11/099,141, Response filed Aug. 20, 2007 to Non Final Office Action mailed May 18, 2007", 11 pgs.

"U.S. Appl. No. 11/099,141, Restriction Requirement mailed Mar. 6, 2007", 6 pgs.

"U.S. Appl. No. 11/125,503, Examiner Interview Summary mailed Oct. 18, 2007", 4 pgs.

"U.S. Appl. No. 11/125,503, Non-Final Office Action mailed Jun. 28, 2007", 8 pgs.

"U.S. Appl. No. 11/125,503, Notice of Allowance mailed Mar. 8, 2007", 8 pgs.

"U.S. Appl. No. 11/125,503, Response filed Oct. 29, 2007 to Non Final Office Action mailed Jun. 28, 2007", 21 pgs.

"U.S. Appl. No. 11/137,038, Appeal Brief mailed Jan. 18, 2010", 35 pgs.

"U.S. Appl. No. 11/137,038, Final Office Action mailed Aug. 14, 2009", 10 pgs.

"U.S. Appl. No. 11/137,038, Final Office Action mailed Aug. 29, 2008", FOAR, 10 pgs.

"U.S. Appl. No. 11/137,038, Non-Final Office Action mailed Feb. 5, 2008", OARN, 8 pgs.

"U.S. Appl. No. 11/312,178, Non-Final Office Action mailed May 14, 2008", 6 pgs.

"U.S. Appl. No. 11/312,178, Notice of Allowance mailed Apr. 3, 2009", 6 pgs.

"U.S. Appl. No. 11/312,178, Notice of Allowance mailed Nov. 14, 2008", 6 pgs.

"U.S. Appl. No. 11/312,178, Preliminary Amendment filed Mar. 14, 2006", 7 pgs.

"U.S. Appl. No. 11/312,178, Response filed Aug. 14, 2008 to Non Final Office Action mailed May 14, 2008", 14 pgs.

"U.S. Appl. No. 11/459,481, Notice of Allowance mailed Nov. 20, 2010", 7 pgs.

"U.S. Appl. No. 11/459,481, Restriction Requirement mailed Jan. 29, 2010", 6 pgs.

(56) References Cited

OTHER PUBLICATIONS

"U.S. Appl. No. 11/459,481, Final Office Action mailed May 17, 2010", 11 pgs.
"U.S. Appl. No. 11/459,481, Non-Final Office Action mailed May 28, 2009", 10 pgs.
"U.S. Appl. No. 11/459,481, Response filed Jan. 29, 2009 to Restriction Requirement mailed Dec. 30, 2008", 10 pgs.
"U.S. Appl. No. 11/459,481, Response filed Feb. 10, 2010 to Restriction Requirement mailed Jan. 29, 2010", 8 pgs.
"U.S. Appl. No. 11/459,481, Response filed Aug. 17, 2010 to Final Office Action mailed May 17, 2010", 9 pgs.
"U.S. Appl. No. 11/459,481, Response filed Nov. 25, 2009 to Non Final Office Action mailed May 28, 2009", 14 pgs.
"U.S. Appl. No. 11/459,481, Restriction Requirement mailed Dec. 30, 2008", 7 pgs.
"U.S. Appl. No. 11/558,083, Response filed Dec. 22, 2009 to Non-Final Office Action mailed Jun. 26, 2009", 15 pgs.
"U.S. Appl. No. 11/868,408, Preliminary Amendment filed Oct. 5, 2007", 2 pgs.
"U.S. Appl. No. 12/148,843, Non Final Office Action mailed May 31, 2011", 8 pgs.
"U.S. Appl. No. 12/148,843, Notice of Allowance mailed Oct. 27, 2011", 10 pgs.
"U.S. Appl. No. 12/148,843, Response filed Aug. 30, 2011 to Non Final Office Action mailed May 31, 2011", 9 pgs.
"U.S. Appl. No. 12/148,843, Response filed Apr. 14, 2011 to Restriction Requirement mailed Mar. 15, 2011", 10 pgs.
"U.S. Appl. No. 12/148,843, Restriction Requirement mailed Mar. 15, 2011", 9 pgs.
"U.S. Appl. No. 12/688,575 , Response filed Nov. 1, 2012 to Non Final Office Action mailed Aug. 1, 2012", 15 pgs.
"U.S. Appl. No. 12/688,575, Non Final Office Action mailed Aug. 1, 2012", 7 pgs.
"U.S. Appl. No. 12/688,575, Notice of Allowance mailed Nov. 27, 2012", 9 pgs.
"U.S. Appl. No. 12/688,575, Response to Restriction Requirement mailed Mar. 30, 2012", 14 pgs.
"U.S. Appl. No. 12/688,575, Restriction Requirement mailed Mar. 30, 2012", 26 pgs.
"U.S. Appl. No. 12/962,168, Response filed Apr. 15, 2013 to Non Final Office Action mailed Dec. 14, 2012", 13 pgs.
"U.S. Appl. No. 12/962,168, Non Final Office Action mailed Dec. 14, 2012", 17 pgs.
"U.S. Appl. No. 12/962,168, Notice of Allowance mailed Jun. 10, 2013", 10 pgs.
"U.S. Appl. No. 13/397,115, Response filed Feb. 19, 2013 to Non Final Office Action mailed Nov. 21, 2012", 13 pgs.
"U.S. Appl. No. 13/397,115, Non Final Office Action mailed Nov. 21, 2012", 10 pgs.
"U.S. Appl. No. 13/397,115, Notice of Allowance mailed Apr. 3, 2013", 6 pgs.
"European Application Serial No. 06752356.3, Office Action mailed Apr. 1, 2008", 6 pgs.
"European Application Serial No. 06752356.3, Response filed Sep. 11, 2008 to Communication mailed Apr. 1, 2008", 17 pgs.
"European Application Serial No. 06827323.4, Communication mailed Jun. 2, 2009", 2 pgs.
"European Application Serial No. 06827323.4, Communication mailed Nov. 12, 2008.", 3 pgs.
"European Application Serial No. 06827323.4, Response filed Apr. 24, 2009 to Communication mailed Nov. 12, 2008", 6 pgs.
"European Application Serial No. 06827323.4, Summons to Attend Oral Proceedings mailed May 19, 2010", 3 pgs.
"European Application Serial No. 06827323.4, Written Submissions filed Sep. 23, 2010", 4 pgs.
"International Application Serial No. PCT/US2006/011446, International Search Report and Written Opinion mailed Aug. 25, 2006", (2006), 14 pgs.
"International Application Serial No. PCT/US2006/017539, International Search Report and Written Opinion mailed Sep. 1, 2006", 12 pgs.
"International Application Serial No. PCT/US2006/017637, International Search Report and Written Opinion mailed Oct. 20, 2006".
"International Application Serial No. PCT/US2006/042727, International Search Report and Written Opinion mailed Apr. 23, 2007", 16 pgs.
"International Application Serial No. PCT/US2010/059252, International Search Report mailed Mar. 2, 2011", 4 pgs.
"International Application Serial No. PCT/US2010/059252, Written Opinion mailed Mar. 2, 2011", 7 pgs.
"Japanese Application Serial No. 2008-511206, Office Action mailed May 17, 2012", With English Translation, 7 pgs.
"Japanese Application Serial No. 2008-511206, Office Action mailed Oct. 30, 2012", With English Translation, 9 pgs.
"Japanese Application Serial No. 2008-511206, Office Action Response filed Mar. 9, 2012", With English Translation, 12 pgs.
"Japanese Application Serial No. 2008-511206, Response mailed Sep. 14, 2012 to Office Action mailed Mar. 9, 2012", With English Claims, 15 pgs.
Andersen, H, et al., "Long-term follow-up of patients from a randomised trial of atrial versus ventricular pacing for sick-sinus syndrome", Lancet, 350(9086), (Oct. 25, 1997), 1210-6.
Benchimol, A, et al., "Cardiac hemodynamics during stimulation of the right atrium, right ventricle, and left ventricle in normal and abnormal hearts", Circulation, 33(6), (Jun. 1966), 933-44.
Bevan, J A, et al., "Postganglionic sympathetic delay in vascular smooth muscle", Journal of Pharmacology & Experimental Therapeutics, 152(2), (May 1966), 221-30.
Bevan, J A, et al., "Sympathetic nerve-free vascular muscle", Journal of Pharmacology & Experimental Therapeutics, 157(1), (Jul. 1967), 117-24.
Bilgutay, A M, et al., "A new concept in the treatment of hypertension utilizing an implantable electronic device: "Baropacer"", Trans Am Soc Artif Intern Organs., 10, (1964), 387-395.
Bilgutay, A M, et al., "Vagal tuning for the control of supraventricular arrhythmias", Surgical Forum, 16, (1965), 151-3.
Bilgutay, A. M, et al., "Vagal tuning. A new concept in the treatment of supraventricular arrhythmias, angina pectoris, and heart failure", Journal of Thoracic and Cardiovascular Surgery, 56(1), (Jul. 1968), 71-82.
Borst, C, et al., "Optimal frequency of carotid sinus nerve stimulation in treatment of angina pectoris", Cardiovascular Research, 8(5), (Sep. 1974), 674-80.
Braunwald, E, et al., "Carotid sinus nerve stimulation in the treatment of angina pectoris and supraventricular tachycardia", California Medicine, 112(3), (Mar. 1970), 41-50.
Braunwald, E, et al., "Relief of angina pectoris by electrical stimulation of the carotid-sinus nerves", New England Journal of Medicine, 277(24), (Dec. 14, 1967), 1278-83.
Chapleau, M W, et al., "Pulsatile activation of baroreceptors causes central facilitation of baroreflex", American Journal of Physiology, 256(6 Pt 2), (Jun. 1989), H1735-41.
Chapleau, M. W., et al., "Contrasting effects of static and pulsatile pressure on carotid baroreceptor activity in dogs", Circulation, vol. 61, No. 5, (Nov. 1987), 648-658.
Coleridge, J C, et al., "Relationship between pulmonary arterial pressure and impulse activity in pulmonary arterial baroreceptor fibres", Journal of Physiology, 158, (Sep. 1961), 197-205.
Coleridge, J C, et al., "The distribution, connexions and histology of baroreceptors in the pulmonary artery, with some observations on the sensory innervation of the ductus arteriosus", Journal of Physiology, 156, (May 1961), 591-602.
Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.
Courtice, G P, et al., "Effect of frequency and impulse pattern on the non-cholinergic cardiac response to vagal stimulation in the toad, *Bufo marinus*", Journal of the Autonomic Nervous System, 48(3), (Aug. 1994), 267-72.

(56) References Cited

OTHER PUBLICATIONS

Dart, Jr., C H, et al., "Carotid sinus nerve stimulation treatment of angina refractory to other surgical procedures", Annals of Thoracic Surgery, 11(4), (Apr. 1971), 348-59.

De Landsheere, D, et al., "Effect of spinal cord stimulation on regional myocardial perfusion assessed by positron emission tomography", American Journal of Cardiology, 69(14), (May 1, 1992), 1143-9.

Dunning, A. J., "Electrostimulation of the Carotid Sinus Nerve in Angina Pectoris", University Department of Medicine, Binnengasthuis, Amsterdam; Printed by Royal VanGorcum, Assen, Netherlands, (1971), 1-92.

Epstein, S. E., et al., "Treatment of angina pectoris by electrical stimulation of the carotid-sinus nerves", New England Journal of Medicine, 280(18), (May 1, 1969), 971-978.

Farrehi, C, "Stimulation of the carotid sinus nerve in treatment of angina pectoris", American Heart Journal, 80(6), (Dec. 1970), 759-65.

Feliciano, L, et al., "Vagal nerve stimulation releases vasoactive intestinal peptide which significantly increases coronary artery blood flow", Cardiovascular Research, 40(1), (Oct. 1998), 45-55.

Fromer, M, et al., "Ultrarapid subthreshold stimulation for termination of atrioventricular node reentrant tachycardia", Journal of the American College of Cardiology, 20(4), (Oct. 1992), 879-83.

Grassi, Guido, et al., "Baroreflex and non-baroreflex modulation of vagal cardiac control after myocardial infarction", Am J Cardiol., 84(5), (Sep. 1, 1999), 525-529.

Griffith, Lawrence S.C., et al., "Electrical Stimulation of the Carotid Sinus Nerve in Normotensive and Renal Hypertensive Dogs", Circulation, 28, (Jul.-Dec. 1963), 730.

Henning, R J, et al., "Effects of autonomic nerve stimulation, asynchrony, and load on dP/dtmax and on dP/dtmin", American Journal of Physiology, 260(4 Pt 2), (Apr. 1991), H1290-H1298.

Henning, R J, et al., "Vagal nerve stimulation increases right ventricular contraction and relaxation and heart rate", Cardiovascular Research, 32(5), (Nov. 1996), 846-53.

Henning, R J, et al., "Vagal stimulation attenuates sympathetic enhancement of left ventricular function", American Journal of Physiology, 258(5 Pt 2), (May 1990), H1470-5.

Holmgren, C., et al., "Risk of interference from transcutaneous electrical nerve stimulation on the sensing function of implantable defibrillators", Pacing Clin Electrophysiol., 31(2), (Feb. 2008), 151-8.

Hood Jr., W B, et al., "Asynchronous contraction due to late systolic bulging at left ventricular pacing sites", American Journal of Physiology, 217(1), (Jul. 1969), 215-21.

Ishise, H, et al., "Time course of sympathovagal imbalance and left ventricular dysfunction in conscious dogs with heart failure", Journal of Applied Physiology, 84(4), (Apr. 1998), 1234-41.

Jessurun, G A, et al., "Coronary blood flow dynamics during transcutaneous electrical nerve stimulation for stable angina pectoris associated with severe narrowing of one major coronary artery", American Journal of Cardiology, 82(8), erratum appears in Am J Cardiol Feb. 15, 1999;83(4):642, (Oct. 15, 1998), 921-6.

Kandel, Eric R, et al., "Part VII: Arousal, Emotion, and Behavioral Homeostasis", In: Principles of Neural Science, New York : McGraw-Hill, Health Professions Division, (2000), 966-969.

Karpawich, P P, et al., "Altered cardiac histology following apical right ventricular pacing in patients with congenital atrioventricular block", Pacing Clin Electrophysiol., 22(9), (Sep. 1999), 1372-7.

Leclercq, C, et al., "Hemodynamic importance of preserving the normal sequence of ventricular activation in permanent cardiac pacing", Am Heart J., 129(6), (Jun. 1995), 1133-41.

Leutmezer, F, et al., "Electrocardiographic Changes at the onset of Epileptic Seizures", Epilepsia, 44(3), (2003), 348-354.

Levy, M. N., et al., "Effects of Repetitive Bursts of Vagal Activity on Heart Rate", Circulation Research, 30(2), (1972), 186-195.

Li, M., et al., "Vagal nerve stimulation markedly improves long-term survival after chronic heart failure in rats", Circulation, 109(1), (2004), 120-124.

Mannheimer, C, et al., "Epidural spinal electrical stimulation in severe angina pectoris", British Heart Journal, 59(1), (Jan. 1988), 56-61.

Mannheimer, C, et al., "Transcutaneous electrical nerve stimulation (TENS) in angina pectoris", Pain, 26(3), (Sep. 1986), 291-300.

Mannheimer, C, et al., "Transcutaneous electrical nerve stimulation in severe angina pectoris", European Heart Journal, 3(4), (Aug. 1982), 297-302.

Martin, P., "Time-dependent heart period and contractility responses to successive brief vagal stimuli", Am J Physiol, 239(4), (Oct. 1980), H494-H500.

Mazgalev, T N, et al., "Autonomic modification of the atrioventricular node during atrial fibrillation: role in the slowing of ventricular rate", Circulation, 99(21), (Jun. 1, 1999), 2806-14.

McGregor, A., et al., "Right-Sided Vagus Nerve Stimulation as a Treatment for Refractory Epilepsy in Humans", Epilepsia; 46(1), (Jan. 2005), 91-96.

Millar-Craig, M W, et al., "Circadian variation of blood-pressure", Lancet, 1(8068), (Apr. 15, 1978), 795-7.

Minisi, A J, et al., "Regional left ventricular deafferentation increases baroreflex sensitivity following myocardial infarction", Cardiovasc Res., 58(1), (Apr. 1, 2003), 136-41.

Murphy, D F, et al., "Intractable angina pectoris: management with dorsal column stimulation", Medical Journal of Australia, 146(5), (Mar. 2, 1987), 260.

Neistadt, A, et al., "Effects of electrical stimulation of the carotid sinus nerve in reversal of experimentally induced hypertension", Surgery, 61(6), (Jun. 1967), 923-31.

Nolan, J., et al., "Prospective Study of Heart Rate Variability and Mortality in Chronic Heart Failure: Results of the United Kingdom Heart Failure Evaluation and Assessment of Risk Trial (UK-Heart).", Circulation, 98(15), (1998), 1510-1516.

Peters, T K, et al., "Temporal and spatial summation caused by aortic nerve stimulation in rabbits. Effects of stimulation frequencies and amplitudes", Journal of the Autonomic Nervous System, 27(3), (Aug. 1989), 193-205.

Peters, T K, et al., "The principle of electrical carotid sinus nerve stimulation: a nerve pacemaker system for angina pectoris and hypertension therapy", Annals of Biomedical Engineering, 8(4-6), (1980), 445-458.

Philbin, D M, et al., "Inappropriate shocks delivered by an ICD as a result of sensed potentials from a transcutaneous electronic nerve stimulation unit", Pacing & Clinical Electrophysiology, 21(10), (Oct. 1998), 2010-1.

Prakash, P, et al., "Asymmetrical distribution of aortic nerve fibers in the pig", Anat Rec., 158(1), (May 1967), 51-7.

Rosenqvist, M, et al., "The effect of ventricular activation sequence on cardiac performance during pacing", Pacing and Electrophysiology, 19(9), (1996), 1279-1286.

Rugg-Gunn, F. J, et al., "Cardiac arrhythmias in focal epilepsy: a prospective long-term study.", Lancet, 364(9452), (Dec. 18-31, 2004), 2212-9.

Rushmer, Robert F, "Chapter 5—Systemic Arterial Pressure", In: Cardiovascular dynamics, Philadelphia : Saunders, (1976), 176-216.

Schauerte, P, et al., "Catheter stimulation of cardiac parasympathetic nerves in humans: a novel approach to the cardiac autonomic nervous system", Circulation, 104(20), (Nov. 13, 2001), 2430-5.

Schauerte, P, et al., "Ventricular rate control during atrial fibrillation by cardiac parasympathetic nerve stimulation: a transvenous approach", J Am Coll Cardiol., 34(7), (Dec. 1999), 2043-50.

Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.

Schauerte, P., et al., "Transvenous parasympathetic nerve stimulation in the inferior vena cava and atrioventricular conduction", Journal of Cardiovascular Electrophysiology, 11(1), (Jan. 2000), 1 pg.

Scherlag, M A., et al., "Endovascular Neural Stimulation Via a Novel Basket Electrode Catheter: Comparison of Electrode Configurations", Journal of Interventional Cardiac Electrophysiology, 4(1), (Apr. 2000), 219-224.

Sigurdsson, a., et al., "The Role of Neurohormonal Activation in Chronic Heart Failure and Postmyocardial Infarction", American Heart Journal, 132(1, Part 2), (Jul. 1996), 229-234.

(56) References Cited

OTHER PUBLICATIONS

Takahashi, N, et al., "Vagal modulation of ventricular tachyarrhythmias induced by left ansae subclaviae stimulation in rabbits", Japanese Heart Journal, 39(4), (Jul. 1998), 503-11.

Tse, H F, et al., "Long-term effect of right ventricular pacing on myocardial perfusion and function", J Am Coll Cardiol., 29(4), (Mar. 15, 1997), 744-9.

Vanoli, E., et al., "Vagal Stimulation and Prevention of Sudden Death in Conscious Dogs With a Healed Myocardial Infarction", Circulation Research, 68(5), (May 1991), 1471-1481.

Veerman, D P, et al., "Circadian profile of systemic hemodynamics", Hypertension, 26(1), (Jul. 1995), 55-9.

Verity, M a, et al., "Plurivesicular nerve endings in the pulmonary artery", Nature, 211(48), (Jul. 30, 1966), 537-8.

Verity, M, et al., "Pulmonary artery innervation: a morphopharmacologic correlation", Proceedings of the Western Pharmacology Society, 8, (1965), 57-9.

Wallick, D W, et al., "Selective AV nodal vagal stimulation improves hemodynamics during acute atrial fibrillation in dogs", American Journal of Physiology—Heart & Circulatory Physiology, 281(4), (Oct. 2001), H1490-7.

Waninger, M S, et al., "Electrophysiological control of ventricular rate during atrial fibrillation", Pacing & Clinical Electrophysiology, 23(8), (Aug. 2000), 1239-44.

Wiggers, C J, et al., "The muscular reactions of the mammalian ventricles to artificial surface stimuli", American Journal of Physiology, (1925), 346-378.

Zhang, Y, et al., "Optimal ventricular rate slowing during atrial fibrillation by feedback AV nodal-selective vagal stimulation", American Journal of Physiology—Heart & Circulatory Physiology, 282(3), (Mar. 2002), H1102-10.

Zhou, X, et al., "Prevention of high incidence of neurally mediated ventricular arrhythmias by afferent nerve stimulation in dogs", Circulation, 101(7), (Feb. 22, 2000), 819-24.

U.S. Appl. No. 14/325,634, filed Jul. 8, 2014, System and Method to Deliver Therapy in Presence of Another Therapy.

* cited by examiner

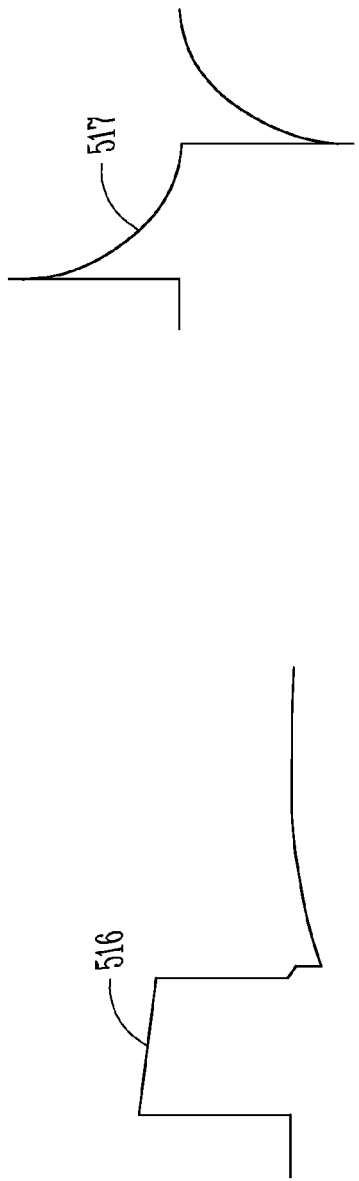
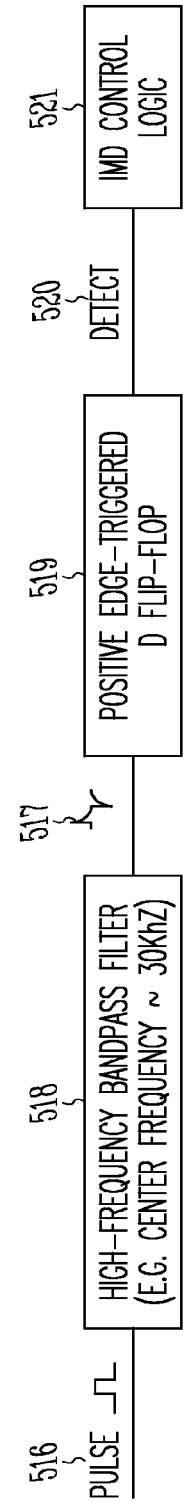
Fig. 5A
Fig. 5B
Fig. 5C

CONCURRENT THERAPY DETECTION IN IMPLANTABLE MEDICAL DEVICES

CLAIM OF PRIORITY

This application is a division of U.S. application Ser. No. 12/962,168, filed Dec. 7, 2010, now issued as U.S. Pat. No. 8,548,585, which claims the benefit of priority under 35 U.S.C. §119(e) of U.S. Provisional Patent Application Ser. No. 61/267,610, filed on Dec. 8, 2009, each of which is herein incorporated by reference in its entirety.

TECHNICAL FIELD

This application relates generally to medical devices and, more particularly, to systems, devices and methods for detecting concurrent therapies.

BACKGROUND

There are a number of implantable medical devices (IMDs) that deliver electrical therapy, and others have been proposed. By way of example and not limitation, IMDs include implantable cardiac rhythm management (CRM) such as cardiac pacemakers, cardioverters, and defibrillators. CRM devices provide electrical stimulation to selected chambers of the heart in order to treat disorders of cardiac rhythm. An implantable pacemaker, for example, is a CRM device that paces the heart with timed pacing pulses. Other IMD examples include spinal cord stimulators, muscle stimulators, and nerve stimulators. For example, it has been proposed to stimulate neural targets (referred to as neural stimulation, neurostimulation or neuromodulation) to treat a variety of pathological conditions. For example, research has indicated that electrical stimulation of the carotid sinus nerve can result in reduction of experimental hypertension, and that direct electrical stimulation to the pressoreceptive regions of the carotid sinus itself brings about reflex reduction in experimental hypertension. Additionally, devices other than implantable devices may deliver electrical stimulation. An example of such devices includes transcutaneous electrical nerve stimulation (TENS) devices.

SUMMARY

Various embodiments of a system for detecting a concurrent electrical therapy applied to a patient comprise an implantable medical device (IMD) configured to be implanted in the patient and configured to detect the concurrent electrical therapy. The concurrent electrical therapy includes a plurality of electrical therapy pulses. The IMD includes a storage, concurrent therapy detection circuitry, and a controller. The storage includes at least one characteristic of the therapy pulses in the concurrent electrical therapy. The concurrent therapy detection circuitry is configured to detect electrical pulses and to extract at least one characteristic of the detected electrical pulses. The controller is configured to compare the at least one characteristic of the detected electrical pulses to the at least one stored characteristic of the therapy pulses and to declare that the concurrent therapy is being applied to the patient if the at least one characteristic of the detected electrical pulses favorably compare to the at least one stored characteristic of the therapy pulses.

Various method embodiments detect a concurrent therapy, where the concurrent therapy includes a plurality of therapy pulses. Detecting the concurrent therapy includes detecting at least one electrical pulse, extracting at least one characteristic from the at least one electrical pulse, comparing the at least one characteristic of the detected pulse to at least one characteristic of therapy pulses, and detecting that the concurrent therapy is being applied if the at least one characteristic of the detected pulse favorably compares to the at least one characteristic of the therapy pulses.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 5A illustrates a pulse, FIG. 5B illustrates the transformed signal of FIG. 5A after pacing through a high-frequency bandpass filter with a center frequency on the order of 30 kHz, and FIG. 5C illustrates an embodiment of a pulse detect circuit.

DETAILED DESCRIPTION

Figure 1:
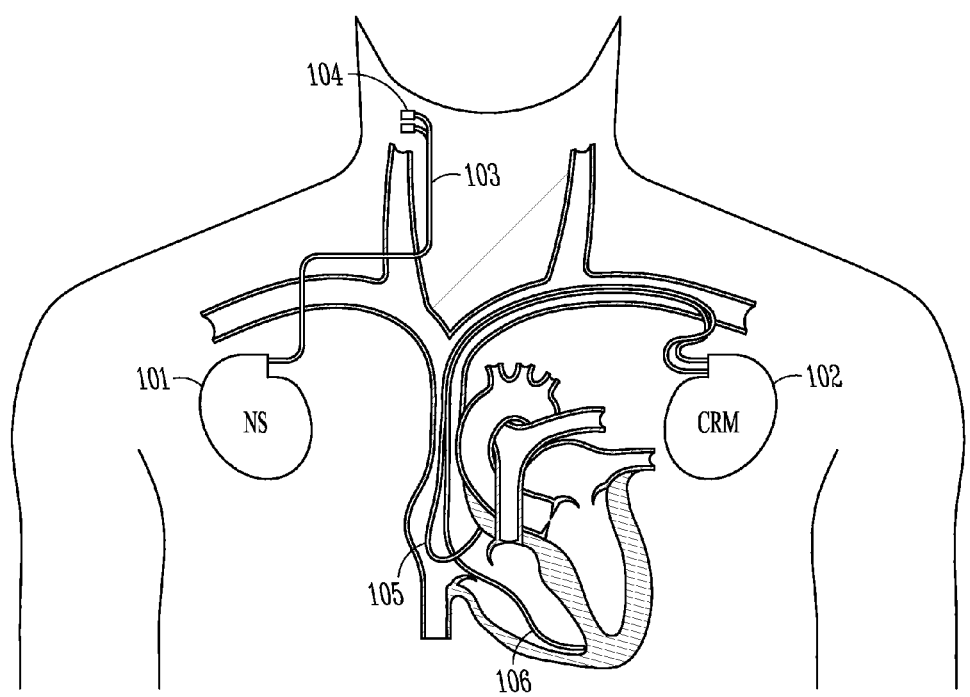
FIG. 1 illustrates a system with an implantable neural stimulator and an implantable CRM device, according to various embodiments

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various IMDs stimulate the autonomic nervous system (ANS), which regulates "involuntary" organs. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force are increased when the sympathetic nervous system is stimulated, and is decreased when the sympathetic nervous system is inhibited (or the parasympathetic nervous system is stimulated). Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intention, increases urine secretion, and contracts the wall and relaxes the sphincter of the bladder. The functions associated with the sympathetic and parasympathetic nervous systems are many and can be complexly integrated with each other.

Vagal modulation may be used to treat a variety of cardiovascular disorders, including but not limited to heart failure, post-MI (myocardial infarction) remodeling, and hypertension. Heart failure refers to a clinical syndrome in which cardiac function causes a below normal cardiac output that can fall below a level adequate to meet the metabolic demand of tissues. Heart failure may present itself as congestive heart failure (CHF) due to the accompanying venous and pulmonary congestion. Heart failure can be due to a variety of etiologies such as ischemic heart disease, hypertension and diabetes. Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. Cardiac remodeling refers to a complex remodeling process of the ventricles that involves structural, biochemical, neurohormonal, and electrophysiologic factors, which can result following an MI or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamics, sympathetic nervous system and hormonal alterations (such as presence or absence of angiotensin converting enzyme (ACE) activity) accounts for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Examples of neural stimulation therapies include neural stimulation therapies for respiratory problems such a sleep disordered breathing, for blood pressure control such as to treat hypertension, for cardiac rhythm management, for myocardial infarction and ischemia, for heart failure, for epilepsy, for depression, for pain, for migraines and for eating disorders and obesity. Many proposed neural stimulation therapies include stimulation of the vagus nerve. This listing of other neural stimulation therapies is not intended to be an exhaustive listing. Electrical neural stimulation of the autonomic system, for example, can be delivered using any of a nerve cuff, intravascularly-fed lead, or transcutaneous electrodes.

A therapy embodiment involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy (ART). When delivered in conjunction with ventricular resynchronization pacing, also referred to as remodeling control therapy (RCT), such modulation of autonomic activity may act synergistically to reverse or prevent cardiac remodeling.

A neural stimulation therapy embodiment treats hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes (e.g. sensory nerve endings that function as a baroreceptor) that is sensitive to stretching of the wall resulting from increased pressure from within, and that functions as the receptor of the central reflex mechanism that tends to reduce that pressure. Baroreflex neural targets also include neural pathways extending from the baroreceptors. Examples of nerve trunks that can serve as baroreflex neural targets include the vagus, aortic and carotid nerves.

A myocardial stimulation therapy provides a cardiac therapy using electrical stimulation of the myocardium. Some examples of myocardial stimulation therapies are provided below. A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A CRT example applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected. ATP may be referred to as overdrive pacing. Other overdrive pacing therapies exist, such as intermittent pacing therapy (IPT), which may also be referred to as a conditioning therapy.

FIG. 1 illustrates a system with an implantable neural stimulator 101 and an implantable CRM device 102, according to various embodiments. For example, the neural stimulator may be configured to stimulate a vagus nerve in the cervical region, as illustrated in the figure. Examples of CRM devices include pacemakers, anti-arrhythmia devices such as defibrillators and anti-tachycardia devices, and devices to deliver cardiac resynchronization therapy (CRT). The illustrated neural stimulator has a neural stimulation lead 103 for use to deliver neural stimulation. The illustrated lead embodiment has a nerve cuff electrode 104. Other lead embodiments provide transvascular stimulation of the nerve (e.g. stimulation of the vagus nerve from the internal jugular vein). In some embodiments, the neural stimulation lead 103 has neural sensing capabilities, and/or sensing capabilities. The illustrated CRM device 102 includes a right atrial lead 105 and a right ventricle lead 106. Other leads, additional leads, or fewer leads may be used for various device embodiments. In some embodiments, the neural stimulator 101 is a vagal nerve stimulator, such as generally illustrated in FIG. 1. In some embodiments, the neural stimulator is a spinal cord stimulator. If a neural stimulator and a CRM device are not designed to communicate with each other, then at least one of the devices includes a concurrent therapy detector, according to various embodiments.

Thus, as is illustrated by the non-exhaustive examples provided above, there are numerous implantable technologies that use electrical stimulation. One individual may have two or more implanted devices providing therapies. Communication systems could be designed and standards created in order to allow for this coordination between implanted systems. However, such communication systems add complexity to the implanted device design and could impact device longevity. In addition, no standards for communicating between implanted medical devices exist or are currently planned.

For example, therapies such as vagal nerve stimulation therapies or spinal cord stimulation therapies can alter cardiac function, which may affect CRM therapies. Identifying these concurrent therapies can provide diagnostic opportunities as well as opportunities to coordinate the CRM therapies in response to the presence of the concurrent therapy. This disclosure discusses an example when CRM therapy is affected by neural stimulation therapy. Those of ordinary skill in the art will understand that CRM therapies may affect neural therapies. More generally, a first electrical therapy may interfere or enhance a second electrical therapy.

Sensing algorithms in implantable medical devices may be compromised when noise within the device sensing channel bandwidth(s) interferes with the sensing functions. Noise sensed by a pacemaker, for example, could be mistaken by the device for a legitimate cardiac event and lead to inhibition of pacing or inappropriate pacing due to tracking of false atrial senses or triggered pacing of false ventricular senses in a cardiac resynchronization therapy (CRT) device Inhibition of pacing could lead to long periods of asystole. Inappropriate pacing could lead to impaired cardiac function or be proarrhythmic. Noise sensed by an implantable cardiac defibrillator (ICD) could cause inappropriate ATP or shock therapy delivery due to mistaken diagnosis of ventricular tachycardia.

Various embodiments modify sensing algorithms (e.g. increase threshold or provide blanking windows) in response to a detected concurrent therapy. However, the present subject matter is not limited to the modification of sensing algorithms, as various embodiments identified below mitigate competition with a concurrent therapy, coordinate a complementary concurrent therapy, provide enhanced diagnostics accounting for the concurrent therapy, or various combinations thereof.

The therapies delivered by the implanted devices may interfere with each other. Examples of interference include inappropriate sensing of the therapy of one implanted device by another implanted device, and competing therapies (e.g. a pacemaker attempting to drive the heart rate higher while a neurostimulator is attempting to reduce the heart rate). Various embodiments of the present subject matter detect concurrent therapy, enabling the coordination of therapies among multiple implanted devices to mitigate these types of interferences.

The therapies delivered by the implanted devices may complement each other. Various embodiments of the present subject matter detect concurrent therapy, to trigger or enable coordination of complementary therapies among multiple implanted devices. One example of complementary therapies involves a pacemaker and a neurostimulator that are implanted in the same patient. If the neurostimulator recognizes the pacemaker, neural therapy can be gated to the timing cycles of the right atrium, right ventricle or left ventricle pacing signal. Another example sets a maximum and minimum heart rate by which neurostimulation could be inhibited or initiated. If an atrial or ventricular tachyarrhythmia event develops, the pacemaker could send out a signal to enable a high level of continuous neurostimulation.

Another example includes a wireless implantable pressure sensor in the pulmonary artery and a neurostimulator implanted in the same patient. The pressure sensor could send out a signal that enables neurostimulation in response to a decompensation event.

The therapies delivered by the implanted devices may not interfere or compliment each other, but may still provide valuable diagnostic information. Various embodiments of the present subject matter detect concurrent therapy and inform the user that the concurrent therapies exist. Various embodiments use one of the devices to be the primary diagnostic gatherer for the implanted devices. One example involves a cardiac device implanted along with a neurostimulator. If the cardiac device recognizes the neurostimulation signal, it can time stamp the presence of the neural pacing. The physician could then run a diagnostic report which divides the data into neurostimulation present or not present. If a favorable improvement is shown when neurostimulation is on, this could lead to programming changes. This could also be automated within the cardiac device.

Figure 2:
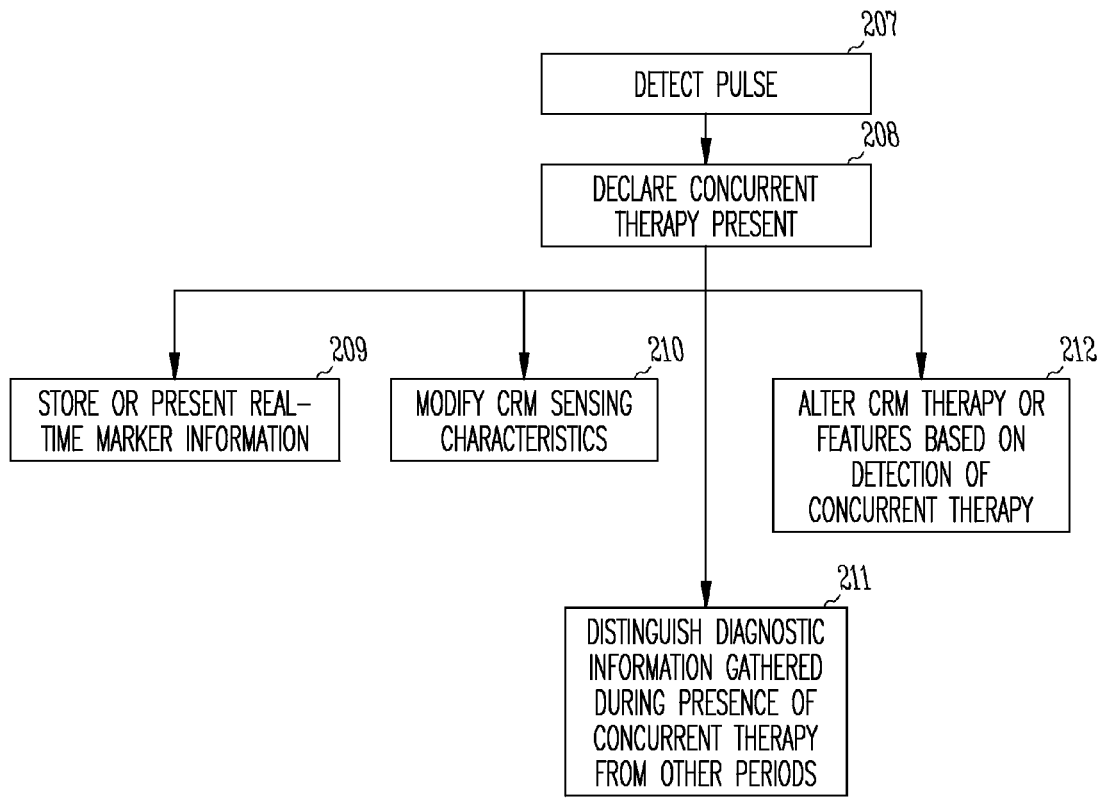
FIG. 2 illustrates various method embodiments.

FIG. 2 illustrates various method embodiments. A pulse is detected at 207. At 208, a concurrent therapy is declared. For example, the concurrent therapy is declared if the detected pulse has characteristics of the pulses used in the concurrent therapy. If it is determined that a concurrent therapy is present, some embodiments store or present real-time marker information 209, some embodiments modify CRM sensing characteristics 210, some embodiments distinguish diagnostic information gathered during the presence of concurrent therapy from the other periods 211, and some embodiments alter CRM therapy or features based on detection of concurrent therapy 212.

According to various embodiments, the present subject matter is capable of detecting multiple therapies from different manufacturers without needing communication circuitry in each device to enable communication between devices and without needing to develop a consensus among implantable device manufacturers around a communication standard. According to various embodiments, sensors and diagnostics are grouped into one primary medical device (e.g. the CRM device by way of example and not limitation), thereby simplifying the secondary medical device and therapy. In some embodiments, each IMD implanted medical device type is designed to identify and adapt to only those electrical therapies that affect its therapy, regardless of the manufacturer of those other electrical therapies.

Various embodiments store or present real-time marker information. Some embodiments convey various levels of detail of the externally or internally delivered concurrent therapy without establishing device-to-device communication, some embodiments modify CRM sensing characteristics. Some embodiments reclassify fast beats associated with detected pulses. Some embodiments remove the fast beats from an ECG and note with a marker. Some embodiments change sensing threshold during presence of detected pulses, extend a blanking period, or extend a refractory, etc. For example, a neural stimulation therapy delivered to an autonomic target can alter cardiac conduction. Therefore, by way of example and not limitation, HRV during the detected concurrent therapy may differ from that when the neural stimulation is not concurrent. Knowledge of this concurrent therapy provides diagnostic insight. By way of another example, AV delays may change during the concurrent therapy which may cause the loss of CRT. This information may be used to appropriately reprogram the device. Thus, various embodiments distinguish diagnostic information gathered during the presence of concurrent therapy from other periods.

Some embodiments change the response of the CRM device when neuromodulation therapy is either recognized or communicated. For example, some embodiments suppress noise, some embodiments use noise response algorithms, some embodiments raise a sensing threshold during a period of neuromodulation therapy, some embodiments alter brady therapy because of physical changes that occur during neuromodulation therapy delivery (immediate term, not long-term like remodeling), and some embodiments alter characteristics or response of other sensors, such as minute ventilation, while neuromodulation therapy is being delivered.

Some examples of adjusting sensing algorithms to accommodate the detected concurrent therapy are provided below. Various embodiments are implemented with separate brady and tachy detection thresholds. The amplitude of "normal" brady sensed P-Waves and R-Waves are typically larger than the amplitudes of tachy sensed atrial or ventricular fibrillation. Tachy therapies are initiated only if a tachycardia event is sensed using the tachy detection threshold and if the bradycardia is lost as sensed using the brady detection threshold The dual threshold approach assumes that normal cardiac function continues in the presence of noise. There are no large R-waves due to PVCs or escape beats when in ventricular fibrillation, muscle noise amplitude is less than P-Wave or R-Wave amplitude, external noise amplitude is less than P-Wave or R-Wave amplitude, and noise response features are still implemented.

For example, a sensing threshold may stairstep down after a sense or pace. The secondary threshold may be consulted during the tachy episode. If the secondary threshold sense detects were within a brady range, the device could declare the episode as noise induced. According to some embodiments, the device responds by delaying shock therapy for 'x' (or indefinite) seconds since noise is generally of limited time as long as ventricular senses are occurring above the secondary threshold at a typical brady rate. Some device embodiments delay shock therapy while pacing the atrial at a lower rate level as long as there are ventricular senses above the secondary threshold. This assumes that normal conduction from an AS or APA is still occurring or that there is a ventricular escape beat. The secondary brady threshold is used to confirm the tachyarrhythmia. Muscle noise and periodic noise can get around current noise detection windows and cause oversensing. A secondary brady threshold protects against inappropriate therapies in such cases.

Some embodiments briefly blank or ignore the signal every period of the noise signal, and some embodiments characterize the periodic signal as noise based on periodicity, width, amplitude, slope, etc., and subtract from the overall signal. Some embodiments include a notation on real-time strip and programmer display that periodic noise has been detected.

Some embodiments respond to a detected arrhythmia by validating that an arrhythmia was detected. An intrinsic event (e.g. sinus node source or escape beat) is monitored during initial detection or reconfirmation. A window timeframe (e.g. around 80 BPM to around 25 BPM range) is created in which to monitor for intrinsic activity This assumes that normal cardiac function continues in the presence of noise, and that there are no large R-waves due to premature ventricular contractions (PVCs) or escape beats when in ventricular fibrillation. This also assumes that both muscle noise amplitude and external noise amplitude is less than P-Wave or R-Wave amplitude.

An autonomic neural stimulation therapy can alter cardiac conduction. Some embodiments are configured to alter CRM therapy, in response to the detection of a concurrent therapy, to tailor the therapy to the individual's medical therapy treatment. For example, the CRM therapy may be altered during the autonomic neural stimulation therapy to use a modified AV delay, use a modified AV delay offset, suspend AV delay search hysteresis, use a modified lower rate limit (LRL), modify the rhythm identification template gathering, and use modified pace amplitudes because of an altered captured threshold.

Not all detectable concurrent therapies directly affect cardiac conduction. Therefore, various embodiments of a CRM system are configured to distinguish between types of concurrent therapy (e.g. pain management versus high blood pressure therapy) and have different responses based on that determination such as markers only for one and modified diagnostic gathering for the other. Various embodiments consolidate information into devices without the need to create device-to-device communications. The CRM therapies respond to the concurrent therapies providing holistic therapy delivery.

As illustrated generally at 207, various embodiments detect a pulse to detect whether a concurrent therapy is present, as generally illustrated at 208. A characteristic of many stimulation pulses is sharp leading and falling edges.

Figure 3:
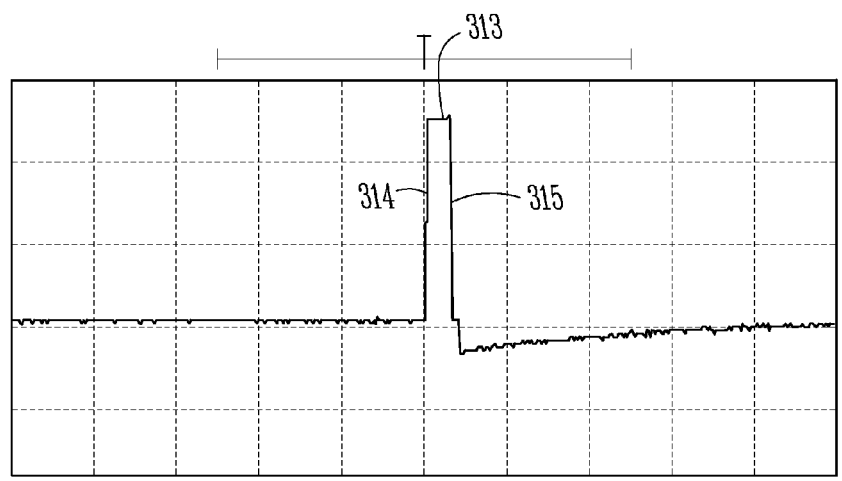
FIG. 3 illustrates an example of a neural stimulation therapy pulse.
Figure 4A:
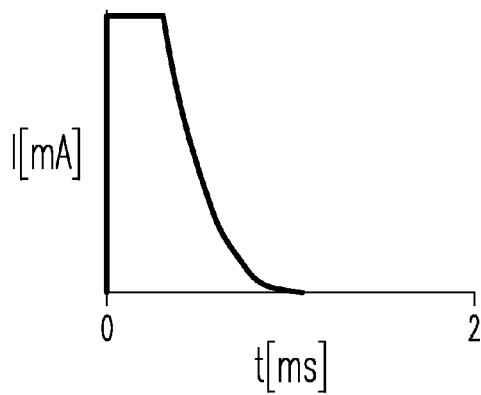
FIG. 4A illustrates a trapezoidal waveform.
Figure 4B:
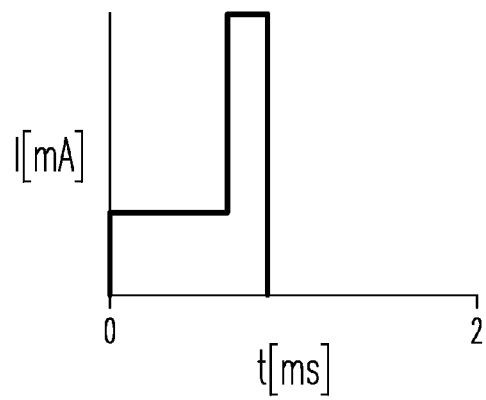
FIG. 4B illustrates a pre-conditioning waveform.
Figure 4C:
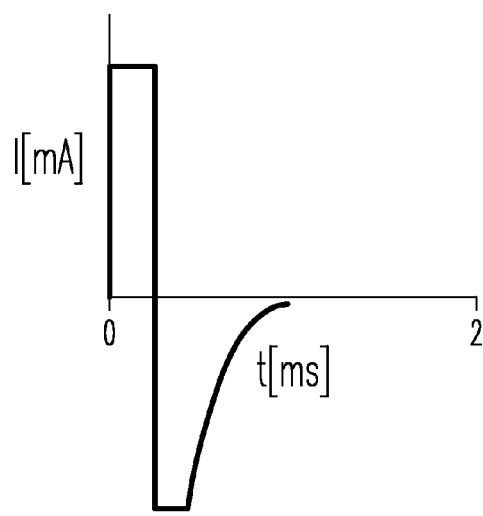
FIG. 4C illustrates a biphasic waveform.

FIG. 3 illustrates an example of a neural stimulation therapy pulse. The illustrated pulse 313 has sharp rising and falling edges, and the sharp transitions at the rising edge 314 and the falling edge 315 of the waveform cause significant high-frequency energy. Other waveforms or pulses have potential for neural stimulation. FIG. 4A illustrates a trapezoidal waveform, FIG. 4B illustrates a pre-conditioning waveform, and FIG. 4C illustrates a biphasic waveform. These waveforms, like the single pulse, have sharp transitions that also cause high-frequency energy. Thus, these waveforms may be detected in a manner similar to that discussed below.

FIG. 5A illustrates a pulse 516. FIG. 5B illustrates the transformed signal 517 of FIG. 5A after pacing through a high-frequency bandpass filter with a center frequency on the order of 30 kHz. The rising edge of the pulse in FIG. 5A results in a positive signal in FIG. 5B that decays during the pulse; and the falling edge of the pulse in FIG. 5A results in a negative signal in FIG. 5B.

FIG. 5C illustrates a pulse detect circuit, including high-frequency band pass filter 518 to receive the pulse 516 and detect the high-frequency components attributable to the sharp rising edge, the sharp falling edge, or both the sharp rising and falling edges of the stimulation signal, as illustrated by the transformed signal 517. In some embodiments, by way of example and not limitation, the output 517 of the high-frequency bandpass filter is fed into processing circuitry 519 such as a positive edge-triggered D flip-flop and logged as a "detect" signal 520. In the illustrated embodiment, the "detect" signal 520 is received by control logic 521 of the IMD to process appropriately. Some embodiments apply various criteria to the pulse to confirm that it is consistent with concurrent therapy pulses. Additionally, FIG. 2, for example, illustrates some ways in which various embodiments of the control logic respond to the detected concurrent therapy. A pre-conditioning waveform or true biphasic waveform would result in a different spike pattern in the output for each pulse, but is conceptually the same. Some embodiments include variable sensing thresholds, discussed below, to reject noise or higher frequency filtering for edge detection. Those refinements will improve detection of concurrent therapies by reducing false detections.

According to various embodiments, the present subject matter uses the pulse detection as a basis for detecting concurrent therapy. Telemetry and other electrical signals such as those used for minute ventilation could confound detection of a concurrent therapy for an amount of time. For some therapies, this amount of time may be inconsequential and, thus, the simpler detection circuitry may be sufficient.

Figure 6:
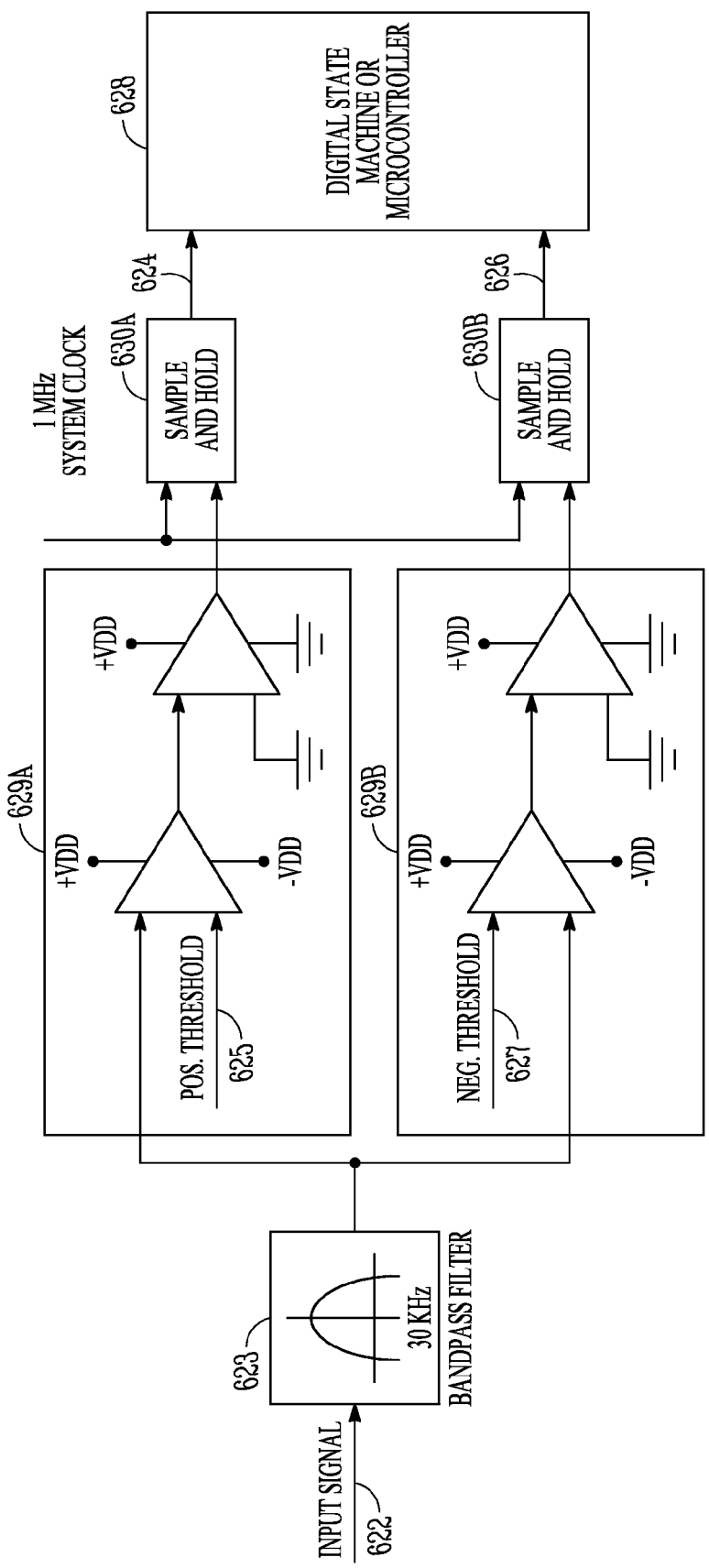
FIG. 6 illustrates an embodiment of remote pace detection circuitry.
Figure 7:
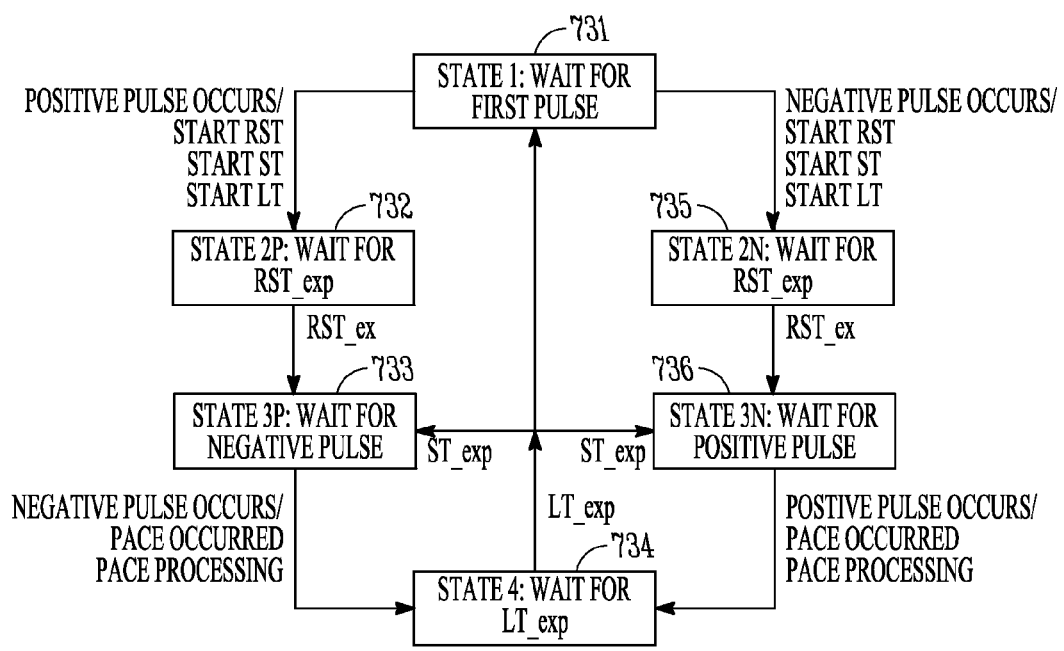
FIG. 7 illustrates a flow diagram of an embodiment for detecting pulses using the pace detection circuitry illustrated in FIG. 6.

FIGS. 6-7 illustrate an embodiment for distinguishing a concurrent therapy from other electrical signals such as telemetry by way of example and not limitation. The output of the high-frequency bandpass includes a paired signal of a positive-going spike and a negative-going spike occurring within a defined time period. The positive spike could lead the negative spike or vice versa depending on the sensing vector in relationship to the signal source and also the polarity of the pulse. For example, a neural stimulation therapy may deliver stimulation pulses with a pulse width ranging from 100 to 1000 µS with 300 µS typical. A pulse detect can be declared if a paired set of spikes occur within the defined pulse width timeframe.

FIG. 6 illustrates an embodiment of remote pace detection circuitry. The input signal 622 comes from sense electrodes, and passes through a bandpass filter 623 illustrated with a center frequency of approximately 30 KHz. The pace detection circuitry creates two detection signals. A first detection signal 624 is generated when the rising edge of a pace pulse passes through the bandpass filter at a level greater than the positive threshold 625. A second detection signal 626 is generated when the falling edge of a pace pulse passes through the bandpass filter at a level more negative than the negative threshold 627. The combination of the two detection signals, as received by the digital state machine or microcontroller 628, results in a pace detection. For each of the illustrated detection signals, the illustrated circuit includes a cascaded amplifier 629A and 629B that functions as a comparator, and a sample and hold circuit 630A and 630B clocked by a 1 MHz system clock.

FIG. 7 illustrates a flow diagram of an embodiment for detecting pulses using the pace detection circuitry illustrated in FIG. 6. State 1, represented at 731, is a state in which the circuit waits for the first pulse. If the first pulse is positive, three timers are started and the circuit enters State 2P, represented at 732. These timers include a first timer identified as a really short timer (RST), a second timer identified as a short timer (ST), and a third timer identified as a long timer (LT). The names given to these timers represent a manner of degree, and are not intended to be limiting. State 2P is a state in which the circuit waits for the first timer (RST) to expire. The end of the time represented by RST represents a beginning of a time frame for an expected negative pulse to occur after the positive pulse sensed at 731. Once the first timer expires, the circuit enters State 3P, represented at 733, which is a state in which the circuit waits for the expected negative pulse. If the second timer (ST) expires without a negative pulse, the circuit returns to State 1 at 731. If a negative pulse occurs, the circuit enters State 4, represented at 734, which is a state in which the circuit waits for the expiration of the third timer (LT). When the third timer (LT) expires, the circuit returns to State 1. If the first pulse is negative, three timers are started and the circuit enters State 2N, represented at 735. These timers include a first timer identified as a really short timer (RST), a second timer identified as a short timer (ST), and a third timer identified as a long timer (LT). The names given to these timers represent a manner of degree, and are not intended to be limiting. Also, the timers associated with the negative pulse may or may not be the same as the timers associated with the positive pulse. State 2N is a state in which the circuit waits for the first timer (RST) to expire. The end of the time represented by RST represents a beginning of a time frame for an expected positive pulse to occur after the negative pulse sensed at 731. Once the first timer expires, the circuit enters State 3N, represented at 736, which is a state in which the circuit waits for the expected positive pulse. If the second timer (ST) expires without a positive pulse, the circuit returns to State 1 at 731. If a positive pulse occurs, the circuit enters State 4, represented at 734, which is a state in which the circuit waits for the expiration of the third timer (LT). When the third timer (LT) expires, the circuit returns to State 1. This algorithm is looking for pulses of opposite polarity that occur between RST and ST apart, where RST and ST are respectively the minimum and maximum expected pacing pulse widths. Once a pace is detected, the algorithm waits a time corresponding to the third timer (LT) from the beginning of the pace before looking for another pulse, where the time corresponding to the third timer (LT) is the expected minimum pulse interval.

Pulse frequency may be used, in place of pulse widths or in addition to pulse widths, to determine the presence of a concurrent therapy. For example, a neural therapy may deliver stimulation pulses with a frequency ranging from 2 Hz to 1200 Hz with 20 Hz typical. Thus, if therapy pulses are being detected every 50 ms, it can be confidently determined that the concurrent therapy is indeed being delivered and that it is being delivered at 20 Hz. In the case that pulse frequency is used alone to detect the presence of the concurrent therapy, the detection of either positive-going spikes or negative-going spikes at the defined consistent frequency will result in the same confidence that a concurrent therapy has been detected with simpler circuitry.

A cardiac pace pulse, for example, can be declared as a concurrent therapy from another implanted medical device by sensing the leading edge of the pulse, the ending edge of the pulse, the timing between leading and ending edges within tolerance of defined interval, or various combinations thereof. Capture could also be confirmed via a wide vector internal electrogram. Some embodiments apply detection criteria. By way of example and not limitation, a cardiac pace pulse will not occur at a rate faster than high pacing limit (e.g. 3 Hz) and anti-tachycardia pacing (ATP) will occur at a rate between a lower ATP limit (3 Hz) and a higher ATP limit (e.g. 20 Hz).

In another example, a neural therapy pulse can be declared as a concurrent therapy by another implanted device by sensing the leading edge of the pulse, the ending edge of the pulse, the timing between leading and ending edges within tolerance of defined interval, or various combinations thereof. To provide more confidence in declaring a neural therapy as a concurrent therapy, some embodiments detect two or more consecutive pulses, or two or more consecutive rising edge detections, or two or more consecutive falling edge detections within tolerance of defined rate.

Figure 8:
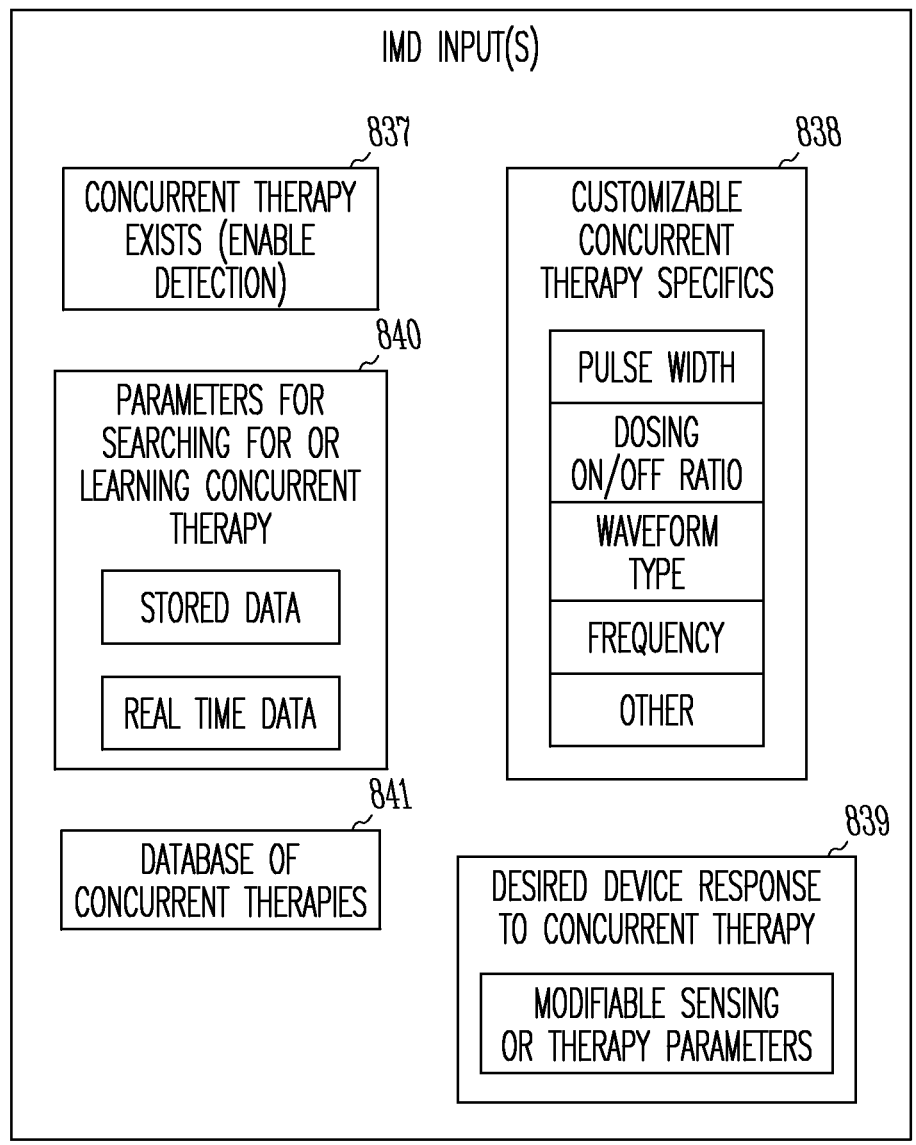
FIG. 8 illustrates potential inputs for various IMD embodiments.

FIG. 8 illustrates potential inputs for various IMD embodiments. These inputs will be discussed in more detail below. The inputs include an enable if it is known that concurrent therapy exists 837, customizable concurrent therapy specifics 838 such as pulse width, dosing on/off ratio, waveform type, frequency or other therapy specifics for the pulses in the therapy, desired device response(s) to the concurrent therapy 839 such as modifying the sensing or therapy parameters, parameters to search for or learn concurrent therapy from either stored or real-time data 840, and a database of concurrent therapies 841.

As there are many potential concurrent therapies that may be delivered by many implantable medical devices, and as these therapies have different waveforms and frequencies, it is difficult to characterize all of the waveforms and frequencies of the possible concurrent therapies currently available much less predict those that will be implemented in the future. However, because the patient and their clinicians are likely aware that other devices are implanted in the patient, various embodiments receive concurrent therapy information from a clinician.

For example, in some embodiments, the clinician inputs into the primary implanted device one or more of the following parameters: existence of a concurrent therapy (enable/disable concurrent detection feature) 837 and customizable concurrent therapy specifics 838 such as pulse width, frequency, dosing (off/on ratio), and waveform type. The implanted medical device is able to use the inputted parameters to customize the bandpass filtering, the pulse width criteria, the frequency criteria and any other criteria explicitly to detect the known concurrent therapy using the detection techniques previously described. This flexibility in the design allows the device to adapt to a manufacturer's concurrent therapy without prior knowledge during design of the details of that concurrent therapy. The clinician is able to confirm that the implanted device is accurately determined by the presence of a concurrent therapy after input of the above parameters.

In addition, the clinician can enter a desired device response 839 to the detected concurrent therapy. Examples of such responses include but are not limited to diagnostic acknowledgement of a detected concurrent therapy (e.g. markers), mitigations for oversensing of concurrent therapy, enhanced diagnostics that distinguish between periods when the concurrent therapy is ON and when the concurrent therapy is OFF, closed-loop of therapy tied to onset of detected concurrent therapy, closed-loop of therapy tied to cessation of detected concurrent therapy, closed-loop of therapy tied to presence of detected concurrent therapy, and modified therapy parameters during presence of detected concurrent therapy Some embodiments modify sensing parameters, such as may be used for a triggering event to begin, end or change a therapy, or as may be used to provide a closed loop feedback for the therapy.

It may be difficult for the clinician to supply the critical parameters needed to customize the detection of a concurrent therapy, as the clinician may not know the details of the concurrent therapy because the device was implanted by another or because of other reasons. However, the patient and their clinicians are likely aware of the fact that other device(s) are implanted. According to various embodiments, the implanted device is configured to respond to a clinician instruction to search for any concurrent therapy. As generally illustrated at 840, the device or the device's supporting external equipment such as a programmer is configured to gather sensed electrical data for a period of time (one minute by way of example and not limitation) and analyze that data for a concurrent therapy. Some embodiments look for the sharp edges characteristic of a concurrent therapy waveform, determine a therapy waveform pulse width, and determine a therapy pulse frequency. The bandpass filtering, the pulse width criteria, the frequency criteria and any other criteria explicitly to detect the known concurrent therapy can be entered or adjusted for the concurrent therapy that has been characterized via this clinician-initiated process. The clinician can confirm that the implanted device is accurately determined by the presence of a concurrent therapy after input of the above parameters. The concurrent therapy may be initiated before and delivered during the time when the device is searching for the concurrent delivery. The clinician may initiate the concurrent therapy just prior to instructing the device to search for the concurrent therapy, or initiate the concurrent therapy while the device is searching.

The clinician may select from the gathered sensed electrical data (real-time data or from stored data) either the period of time there is a concurrent therapy or a pulse from the concurrent therapy. The device or the device's supporting external equipment is configured to analyze this sensed data. Some embodiments look for the sharp edges characteristic of a concurrent therapy waveform, determine a therapy waveform pulse width, determine a therapy pulse frequency, or various combinations thereof.

The bandpass filtering, the pulse width criteria, the frequency criteria and other criteria explicitly may be programmed or modified to detect the known concurrent therapy using the concurrent therapy that has been characterized via this clinician-initiated process. The clinician may confirm that the implanted device is accurately determined by the presence of a concurrent therapy after input of the above parameters.

Thus, the concurrent therapy can be learned and characterized for use by the implanted medical device to detect the concurrent therapy. The clinician can program or input how the device responds to a detected concurrent therapy. Some embodiments provide a trigger for the device to characterize concurrent therapy. The trigger could be a magnet or other user-applied external trigger. This addresses a situation where the concurrent therapy is implanted at a later date and the clinician is not available to reprogram or characterize. The trigger could be a consistent noise window extension or a tachy detection with certain criteria (i.e. very periodic senses indicating oversensing of the concurrent therapy). This addresses a situation where there is concern that the concurrent therapy could adversely affect the primary implanted device but there is a reluctance to alter that primary implanted device's sensing or therapy characteristics unless needed.

Figure 9:
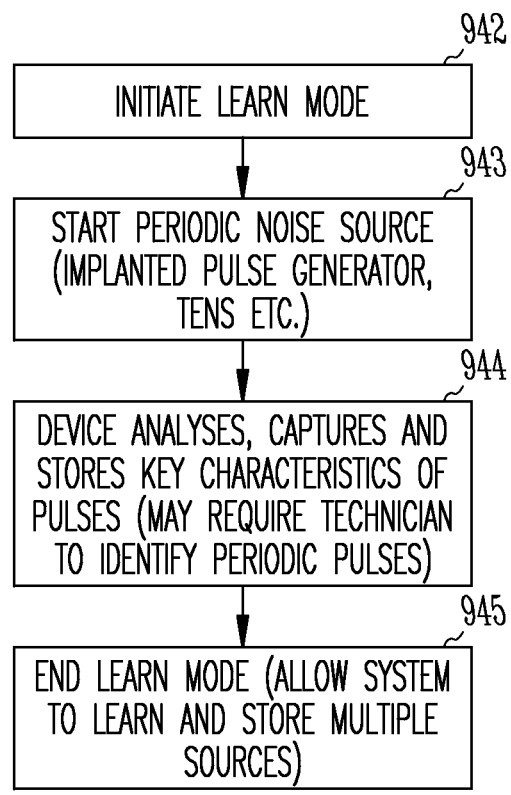
FIG. 9 illustrates an embodiment of a method for performing a learn mode to characterize a stimulation waveform for a concurrent therapy.

FIG. 9 illustrates an embodiment of a method for performing a learn mode to characterize a stimulation waveform for a concurrent therapy. At 942, a learn mode is initiated. This may be initiated by the clinician, for example. The periodic noise source (other concurrent therapy delivered by a TENS system or an IMD, for example) is started at 943. At 944, the device analyses, captures and stores characteristic s of the pulses that can be used to distinguish the pulses from other electrical signals. The learn mode ends at 945. The learn mode can be repeated to learn other sources of potential concurrent therapy.

Figure 11:
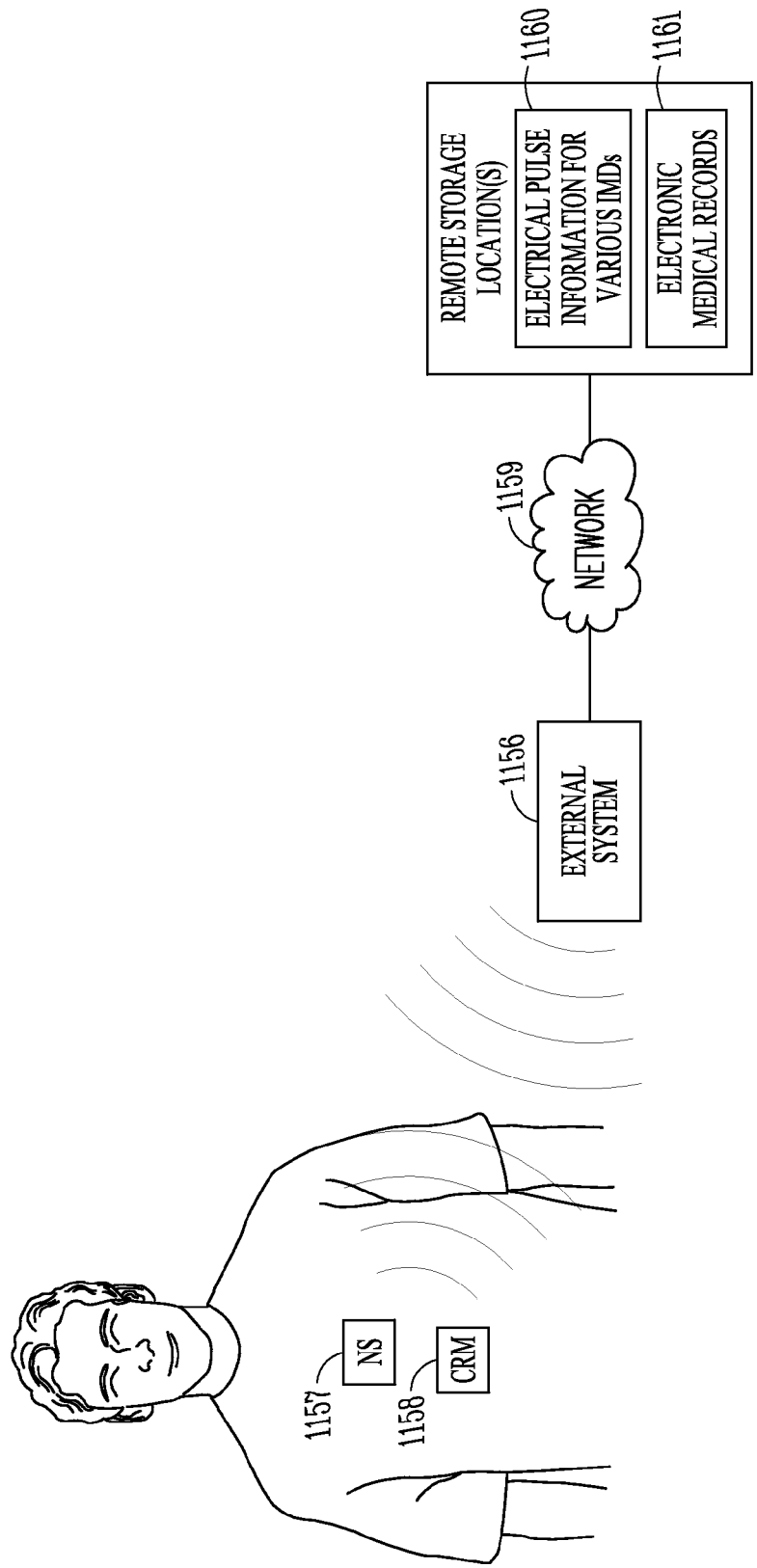
FIG. 11 illustrates a system with the IMD and with external database devices.

With reference to FIG. 11 with FIG. 8, various embodiments use a database 840 containing the electrical pulse characteristics of potential concurrent therapies. According to various embodiments, the primary device's supporting external equipment 1156 such as the programmer is programmed with a database containing the electrical pulse characteristics of specific other secondary devices (e.g. neural stimulation device 1157). A clinician enters the secondary device's identifying information, such as manufacturer and model number, into the programmer of the primary device (e.g. CRM device 1158). The programmer programs the relevant information for characterizing and detecting the concurrent therapy into the implanted device (e.g. the primary device for the two or more implanted devices). If the primary device's programmer supports a connection to an external database via an Internet connection or some other network 1159, the programmer could download the relevant information from the external database 1160, illustrated as electrical pulse information for various IMDs in a remote storage location, rather than being required to keep information for all devices stored on the programmer. If the external database server is integrated with or is capable of connecting to electronic medical records (EMR) systems 1161, the external database server could download not only the secondary device's electrical characteristics, but also details of that specific patient's therapy delivered by the secondary device. These details of the patient's specific therapy may result in a more accurate and consistent coordination of therapies between devices.

Figure 10:
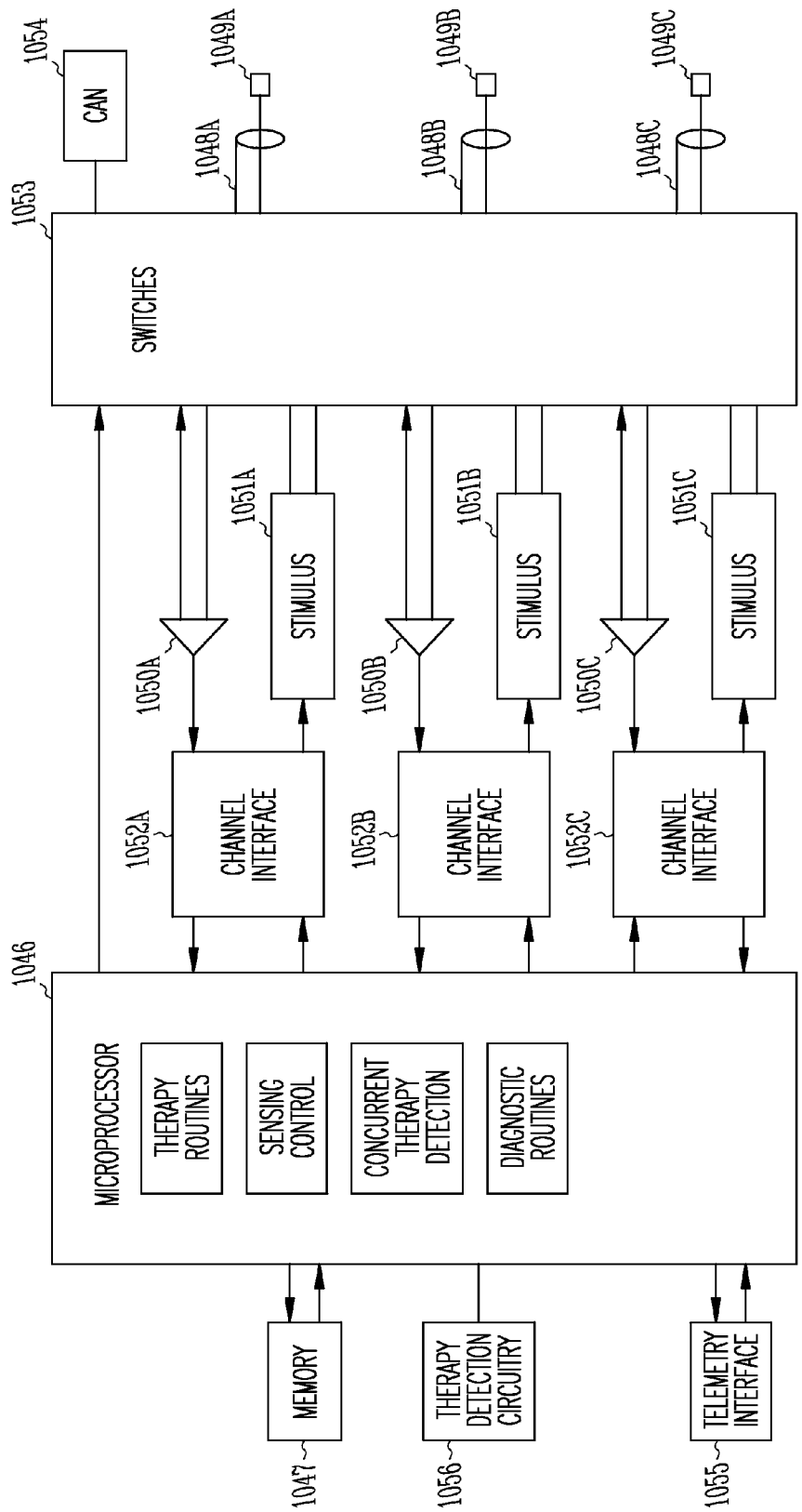
FIG. 10 shows a system diagram of an embodiment of a microprocessor-based implantable device, according to various embodiments.

FIG. 10 shows a system diagram of an embodiment of a microprocessor-based implantable device, according to various embodiments. The controller of the device is a microprocessor 1046 which communicates with a memory 1047 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1048A-C and tip electrodes 1049A-C, sensing amplifiers 1050A-C, stimulus or pulse generators 1051A-C, and channel interfaces 1052A-C. Each channel thus includes a pacing channel made up of the pulse generator connected to the electrode and a sensing channel made up of the sense amplifier connected to the electrode. The channel interfaces 1052A-C communicate bidirectionally with the microprocessor 1046, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1053 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1054 or an electrode on another lead serving as a ground electrode.

The figure illustrates a telemetry interface 1055 connected to the microprocessor, which can be used to communicate with an external device. The microprocessor 1046 is capable of performing therapy routines (e.g. CRM therapy or neural stimulation therapy), and is also configured to control sensing (e.g. thresholds, timing, verification of sensed events). The illustrated system include therapy detection circuitry 1056 to detect pulses of a concurrent therapy, and the microprocessor is capable of performing concurrent therapy detection routines to analyze signals and declare whether or not a concurrent therapy is present. The therapy detection circuitry is configured to detect electrical pulses and configured for use to extract at least one characteristic of the detected electrical pulses. For example, some therapy detection circuitry embodiments are configured for use to extract pulse width or pulse frequency information from the detected pulses. Some therapy detection circuitry includes a high frequency filter to detect pulse edges. The microprocessor, for example, can use this information to detect pulse widths between rising and falling edges of the pulses and to detect pulse frequency. The microcontroller is also capable of performing diagnostic routines. In various embodiments, the microcontroller is capable of responding to a detected concurrent therapy by initiating or adjusting therapy, by initiating or adjusting sensing, or by initiating or adjusting diagnostic routines. Examples of myocardial therapy routines, but are not limited to, include bradycardia pacing therapies, anti-tachycardia shock therapies such as cardioversion or defibrillation therapies, anti-tachycardia pacing therapies (ATP), and cardiac resynchronization therapies (CRT).

FIG. 10 illustrated a microprocessor-based implantable device configured to deliver CRM therapy. Those of ordinary skill in the art will appreciate that a similar device may be configured to deliver neural stimulation therapy. For example, the device is configured to deliver trains of pulses to elicit a desired action potential in a nerve. Some embodiments use nerve cuffs for the nerve electrodes, and some embodiments provide intravascular electrodes for stimulation of neural targets within the vessel (e.g. baroreceptors or chemoreceptors) or for transvascular stimulation of extravascular neural targets such as nerve trunks passing the vessel. Examples of neural stimulation routines include, but are not limited to, therapies to provide physical conditioning and therapies to treat ventricular remodeling, hypertension, sleep disordered breathing, blood pressure control such as to treat hypertension, cardiac rhythm management, myocardial infarction and ischemia, heart failure, epilepsy, depression, for pain, migraines, eating disorders and obesity, and movement disorders. The present subject matter is not limited to a particular therapy.

One of ordinary skill in the art will understand that, the modules and other circuitry shown and described herein can be implemented using software, hardware, firmware and combinations of software and hardware.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a sequence of instructions which, when executed by one or more processors, cause the processor(s) to perform the respective method. In various embodiments, the methods are implemented as a set of instructions contained on a computer-accessible medium such as a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
   detecting a therapy using an implantable device to implement a process, including:
   detecting at least one electrical pulse;
   extracting at least one characteristic from the at least one electrical pulse, wherein the therapy includes therapy pulses with at least one characteristic;
   comparing the at least one characteristic of the detected pulse to the at least one characteristic of the therapy pulses; and
   detecting that the therapy is being applied when the at least one characteristic of the detected pulse favorably compares to the at least one characteristic of the therapy pulses.

2. The method of claim 1, wherein detecting the at least one electrical pulse includes detecting a rising edge or a falling edge of the electrical pulse.

3. The method of claim 2, wherein detecting the rising edge or the falling edge of the electrical pulse includes detecting both the rising edge and the falling edge of the electrical pulse.

4. The method of claim 2, wherein detecting the rising edge or a falling edge of the electrical pulse includes applying a high frequency filter to transform a sensed pulse signal into a transformed signal, wherein the transformed signal has spikes corresponding to transitions at the rising and falling edges of the sensed pulse.

5. The method of claim 4, wherein extracting includes extracting a pulse width from the at least one electrical pulse, and comparing the at least one characteristic of the detected pulse to at least one characteristic of the therapy pulses includes comparing the pulse width of the detected pulse to a pulse width of the therapy pulses.

6. The method of claim 4, wherein extracting includes extracting a pulse frequency from the at least one electrical pulse, and comparing the at least one characteristic of the detected pulse to at least one characteristic of the therapy pulses includes comparing the pulse frequency of the detected pulse to a pulse frequency of the therapy pulses.

7. The method of claim 4, wherein
   detecting at least one electrical pulse includes detecting a plurality of pulses; and
   comparing at least one characteristic of the detected pulse to at least one characteristic of the therapy pulses includes comparing an on/off ratio for the detected pulses to an on/off ratio for the therapy pulses.

8. The method of claim 4, wherein
   extracting at least one characteristic from the at least one electrical pulse includes extracting a waveform for the at least one electrical pulse; and
   comparing at least one characteristic of the detected pulse to at least one characteristic of the therapy pulses includes comparing the waveform for the detected pulses to a waveform for the therapy pulses.

9. The method of claim 4, further comprising applying therapy detection criteria to the at least one detected pulse, and detecting that the therapy is being applied when both the therapy detection criteria is satisfied and the at least one characteristic of the detected pulse favorably compares to the at least one characteristic of the therapy pulses.

10. The method of claim 1, further comprising storing or presenting marker information to identify that the therapy is being applied.

11. The method of claim 1, wherein the therapy is a first electrical therapy, the method further comprising delivering another electrical therapy, wherein delivering the other electrical therapy includes sensing electrical activity to control the electrical therapy, the method further comprising modifying characteristics for sensing electrical activity when the first electrical therapy is being applied.

12. The method of claim 1, further comprising gathering diagnostic information, and distinguishing between diagnostic information gathered when the therapy is being applied and diagnostic information gathered when the therapy is not being applied.

13. The method of claim 1, wherein the therapy is a first electrical therapy, the method further comprising delivering another electrical therapy, and altering the other electrical therapy when the first electrical therapy is being applied.

14. The method of claim 1, wherein comparing characteristics of the detected pulse to at least one characteristic of therapy pulses includes accessing a database of therapies, wherein the database includes pulse characteristics for at least two potential concurrent therapies.

15. The method of claim 1, further comprising:
   beginning a learning mode to enable an implantable medical device to characterize pulses of a detected electrical signal; and
   storing the characterization of the pulses of the detected electrical signal in the IMD,
   wherein comparing at least one characteristic of the detected pulse to at least one characteristic of therapy pulses includes comparing the at least one characteristic of the detected pulse to at least one of the characteristics of the therapy pulses characterized in the learning mode.

16. A method, comprising:
   detecting a therapy using an implantable device to implement a process including:
   detecting at least one electrical pulse, wherein detecting the at least one electrical pulse includes detecting a rising edge or a falling edge of the electrical pulse;
   extracting at least one characteristic from the at least one electrical pulse, wherein the therapy includes therapy pulses with at least one characteristic;
   comparing the at least one characteristic of the detected pulse to the at least one characteristic of therapy pulses; and
   detecting that the therapy is being applied when the at least one characteristic of the detected pulse favorably compares to the at least one characteristic of the therapy pulses; and
   storing or presenting marker information to identify that the concurrent therapy is being applied.

17. The method of claim 16, wherein the therapy is a first electrical therapy, the method further comprising delivering another electrical therapy, wherein delivering the other electrical therapy includes sensing electrical activity to control the other electrical therapy, the method further comprising modifying characteristics for sensing electrical activity when the first electrical therapy is being applied.

18. The method of claim 16, further comprising gathering diagnostic information, and distinguishing between diagnostic information gathered when the therapy is being applied and diagnostic information gathered when the therapy is not being applied.

19. The method of claim 16, wherein the therapy is a first electrical therapy, the method further comprising delivering another electrical therapy, the method further comprising altering the other electrical therapy when the first electrical therapy is being applied.

20. The method of claim 16, wherein detecting the rising edge or a falling edge of the electrical pulse includes applying a high frequency filter to transform a sensed pulse signal into a transformed signal, wherein the transformed signal has spikes corresponding to transitions at the rising and falling edges of the sensed pulse.

* * * * *